(12) United States Patent
Petersen et al.

(10) Patent No.: US 7,937,829 B2
(45) Date of Patent: May 10, 2011

(54) METHOD FOR MANUFACTURING A CONDUCTIVE GRID FOR ATTACHMENT TO A BLISTER PACKAGE

(75) Inventors: Michael Petersen, Ottawa (CA); Allan Wilson, Ottawa (CA); Mykola Sherstyuk, Ottawa (CA)

(73) Assignee: Intelligent Devices, Inc., Christ Church (BB)

( * ) Notice: Subject to any disclaimer, the term of this patent is extended or adjusted under 35 U.S.C. 154(b) by 862 days.

(21) Appl. No.: 11/878,170

(22) Filed: Jul. 20, 2007

(65) Prior Publication Data
US 2008/0053040 A1    Mar. 6, 2008

(30) Foreign Application Priority Data

Jan. 20, 2005   (CA) ..................................... 2493410

(51) Int. Cl.
*H05K 3/30*   (2006.01)
(52) U.S. Cl. ................. 29/832; 29/842; 29/846; 29/854; 53/396; 340/568.1; 340/590; 181/171; 181/172; 310/313 B; 310/313 R
(58) Field of Classification Search .............. 29/831, 29/832, 842, 846, 854; 53/396; 340/568.1, 340/590; 368/10, 11; 181/171, 172; 235/454, 235/455, 492; 310/313 B, 313 R
See application file for complete search history.

(56) References Cited

U.S. PATENT DOCUMENTS

| 4,617,557 | A | 10/1986 | Gordon |
| 6,244,462 | B1 | 6/2001 | Ehrensvard |
| 6,411,567 | B1 * | 6/2002 | Niemiec et al. ................. 368/10 |
| 6,574,166 | B2 * | 6/2003 | Niemiec ......................... 368/10 |
| 7,113,101 | B2 * | 9/2006 | Petersen et al. ............... 340/590 |

FOREIGN PATENT DOCUMENTS

| CA | 2436131 A1 | 1/2005 |
| WO | 01/30123 A1 | 4/2001 |
| WO | 02/05039 A1 | 1/2002 |
| WO | 03/055769 A1 | 7/2003 |
| WO | 2004/110336 A1 | 12/2004 |

* cited by examiner

*Primary Examiner* — Paul D Kim
(74) *Attorney, Agent, or Firm* — Yancy IP Law, PLLC

(57) ABSTRACT

The Med-ic™ Electronic Compliance Monitor (ECM) addresses the problem of patient non-compliance with prescribed medication. The Med-ic™ ECM provides precise information about the patient's use of blister-packaged medication in clinical research and general pharmacy settings. Using an on-board central processing unit (CPU), the Med-ic™ ECM records the time each tablet or capsule is expelled from the blister package, keeping a record for later analysis. At the time of refilling or follow-up visit, the information is downloaded to the research assistant's, physician's or pharmacist's computer where it can be displayed graphically. The data can be stored for later analysis. Production of a Med-ic™ ECM Tag involves numerous steps. These steps incorporate certain methods and technologies to accomplish their objective, the steps being detailed in the specification.

24 Claims, 34 Drawing Sheets

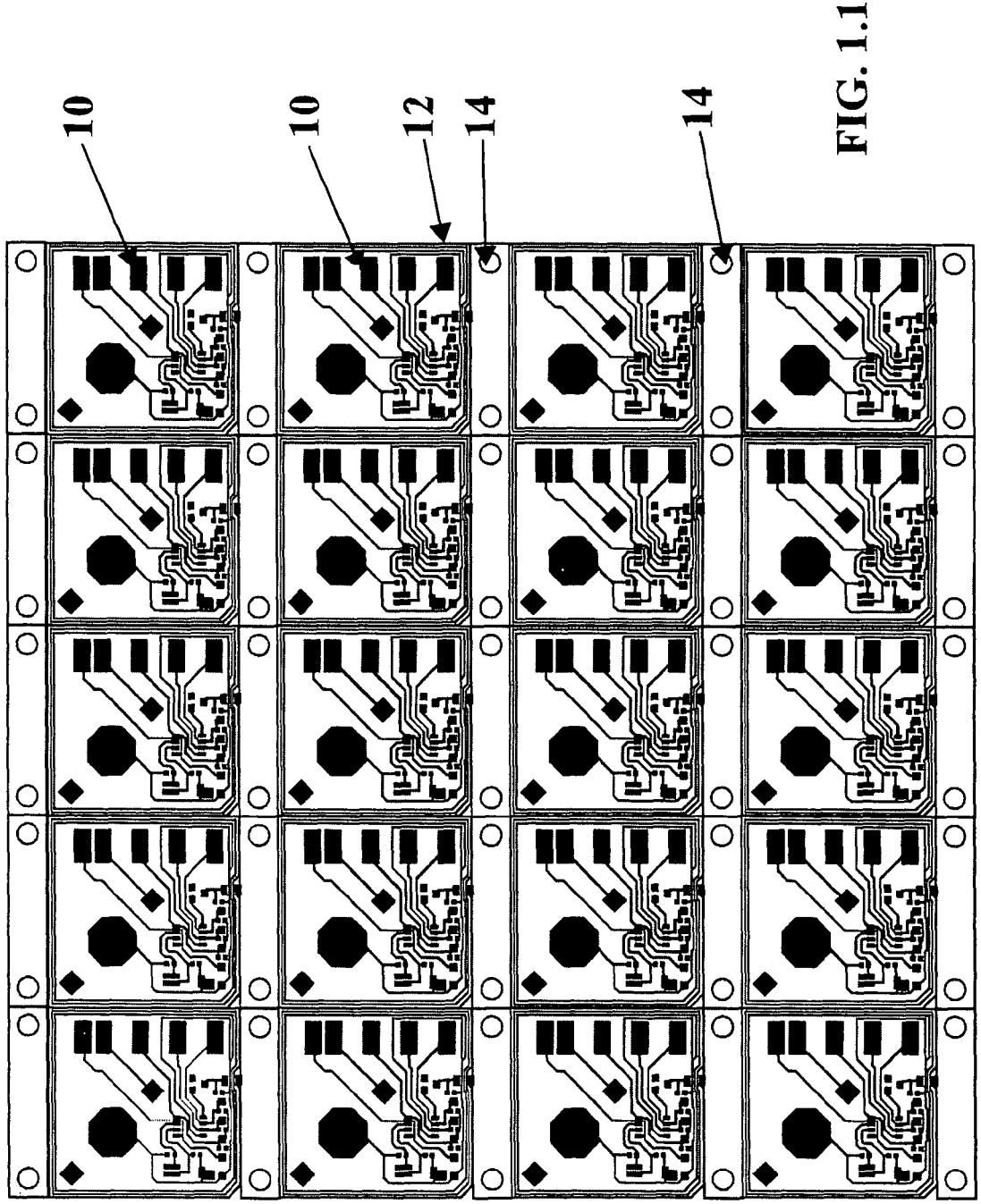

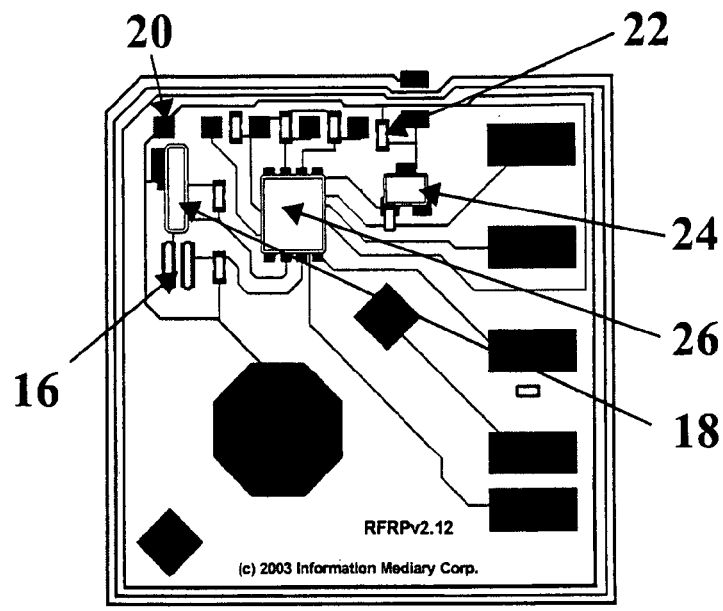
FIG. 2.1
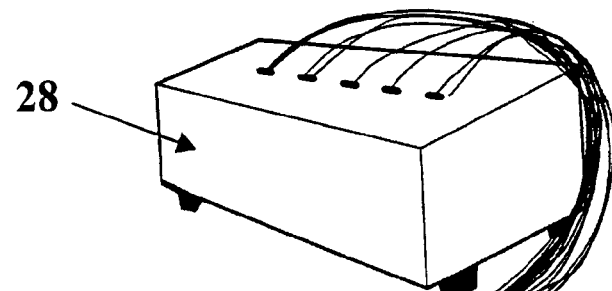
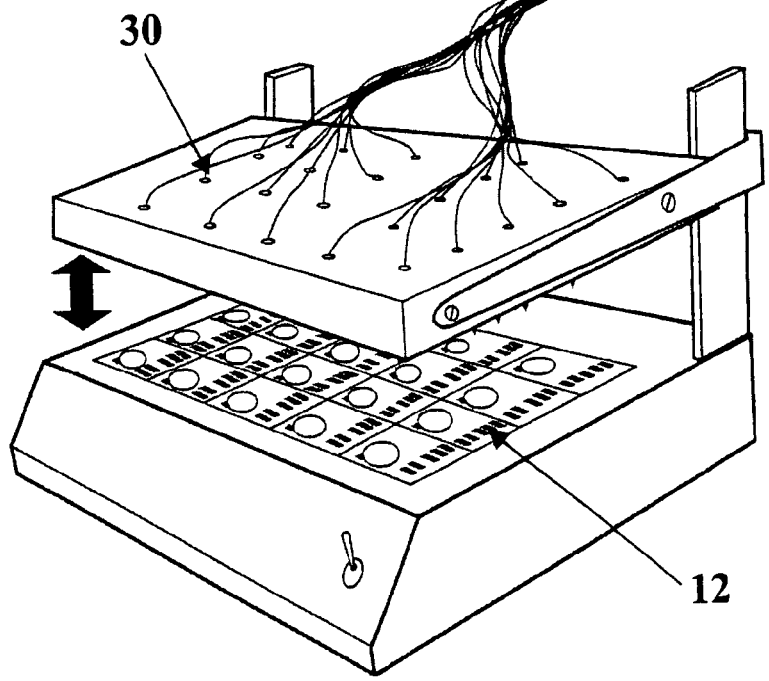
FIG. 3.1

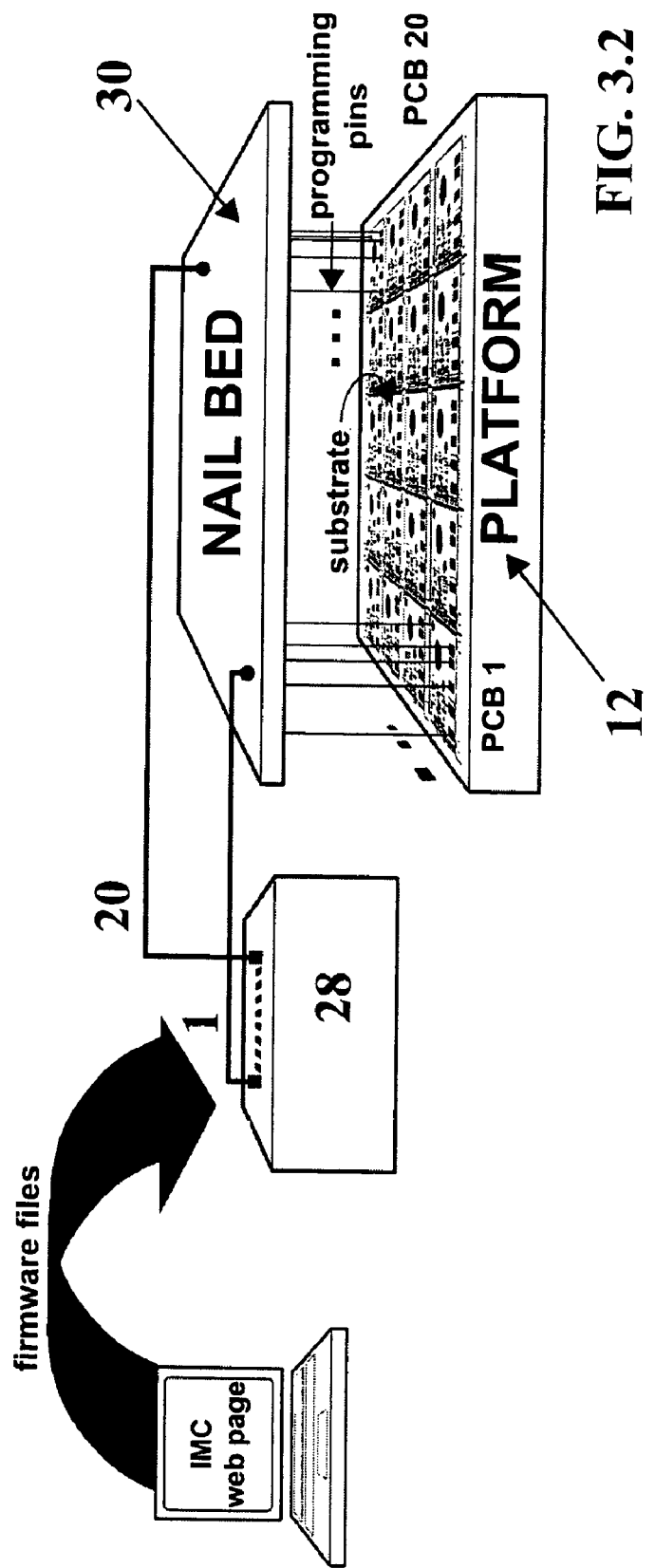
FIG. 3.2

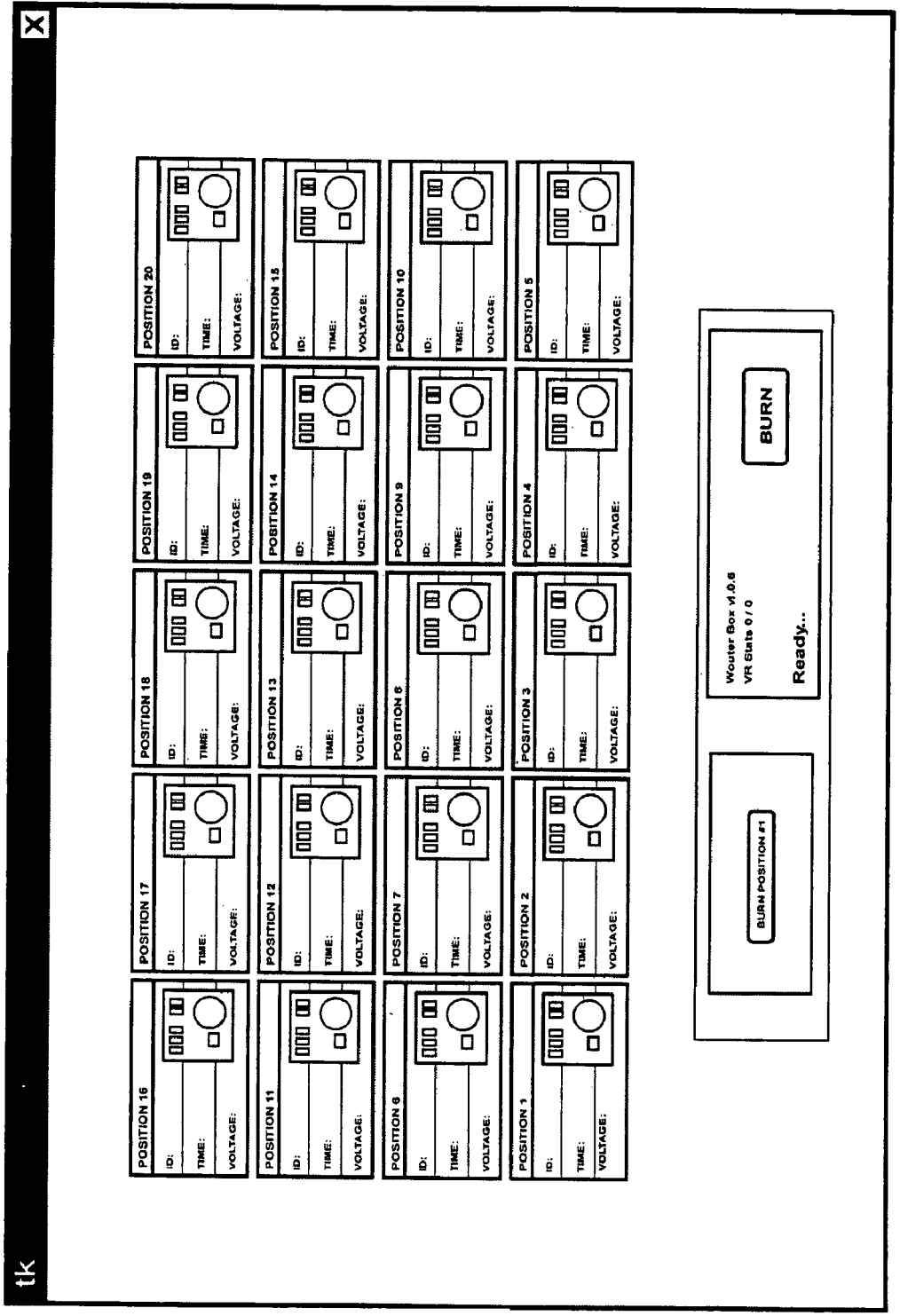
FIG. 3.3

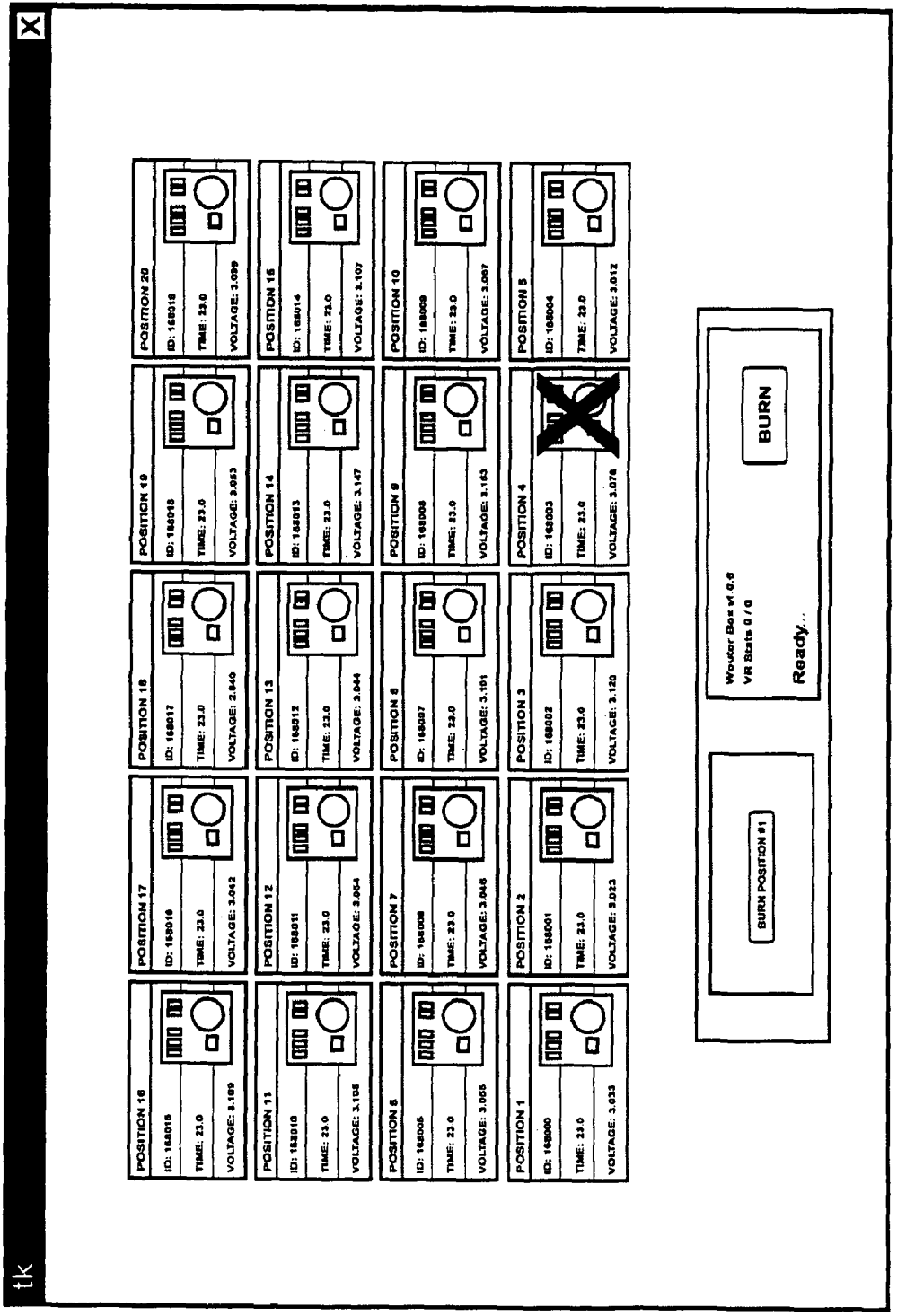
FIG. 3.4

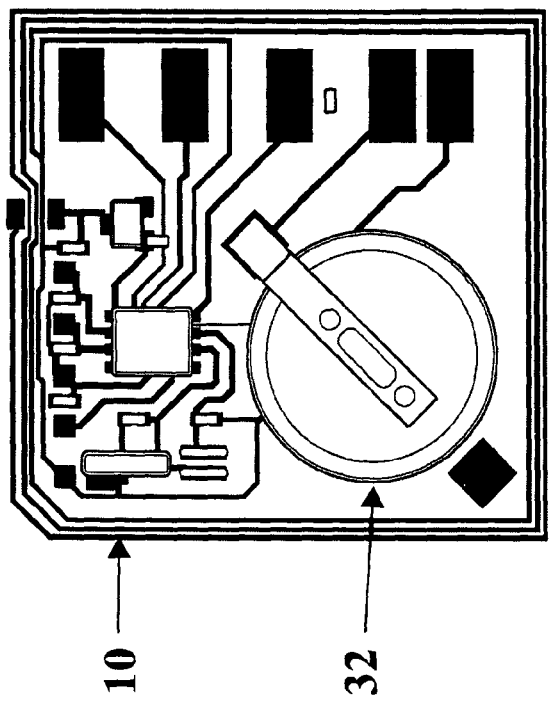
FIG. 4.1
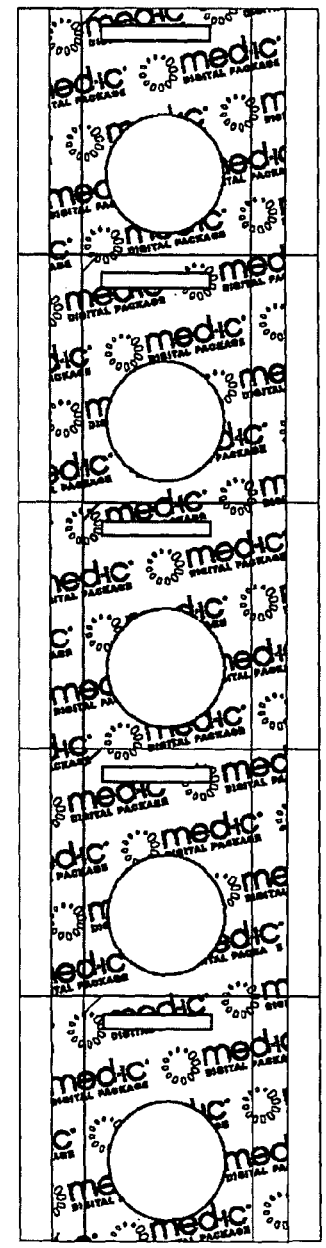
FIG. 5.1 A

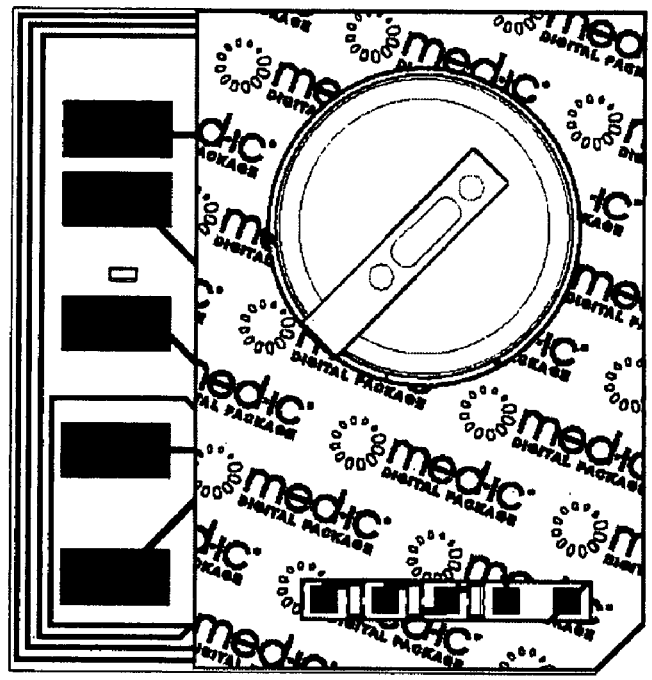
FIG. 5.1 B
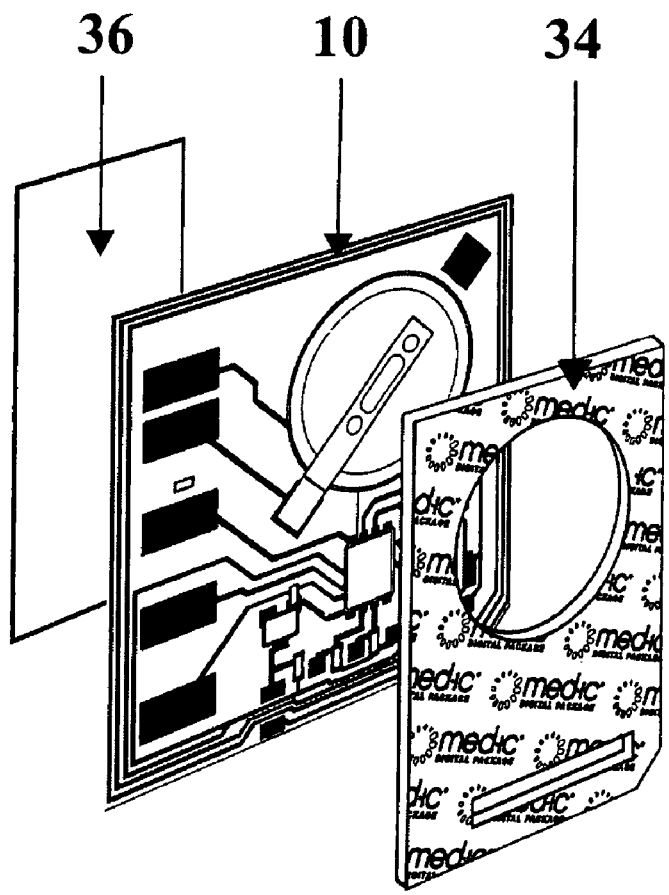
FIG. 6.1

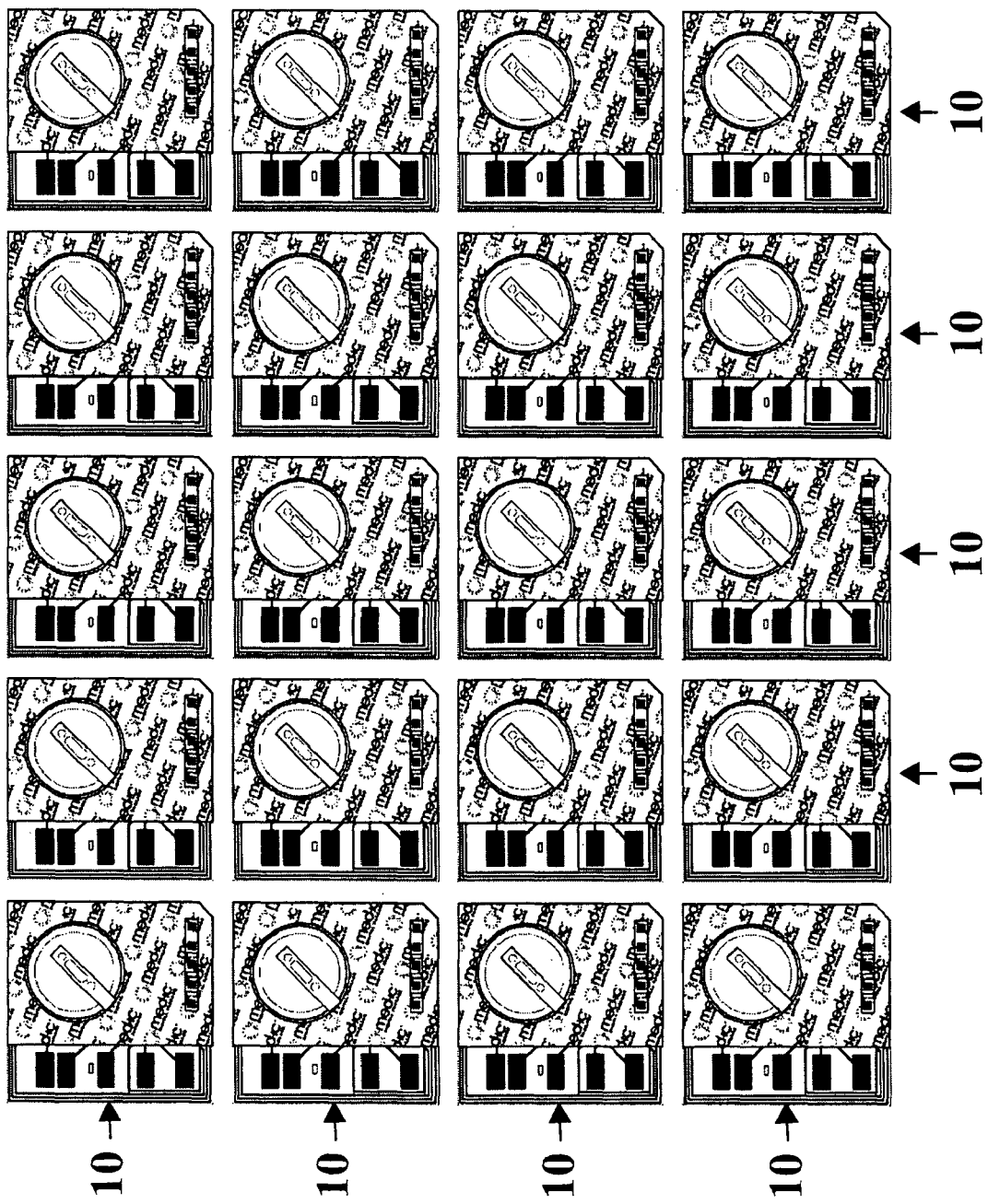
FIG. 7.1

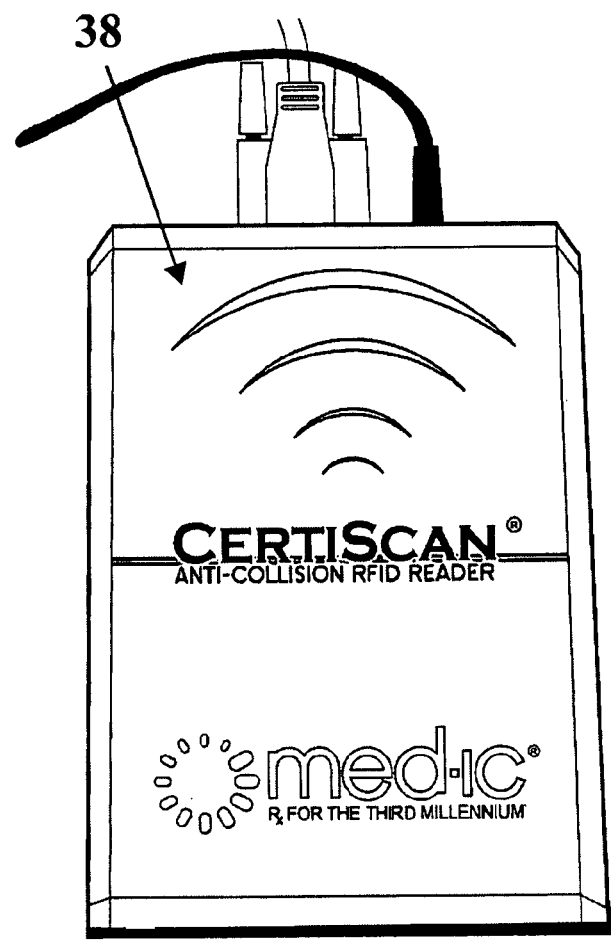
FIG. 8.1 A
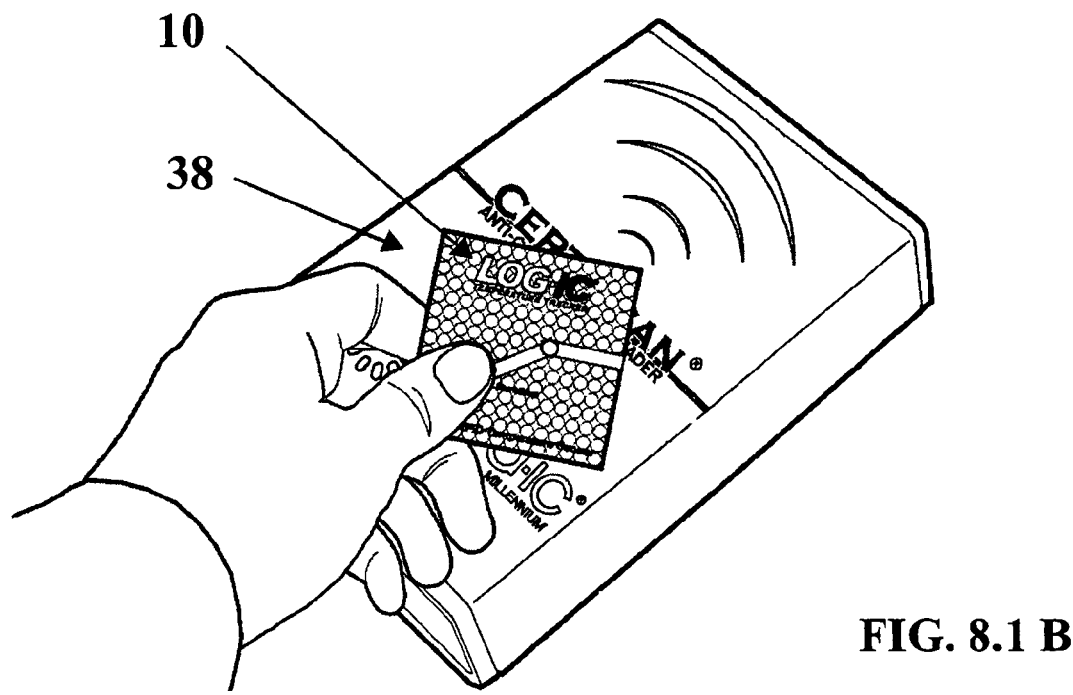
FIG. 8.1 B

QA2 initial screen
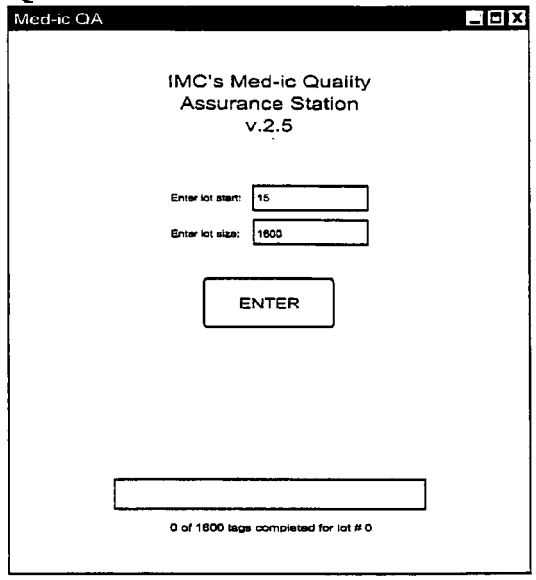
QA2 after Tag scanning
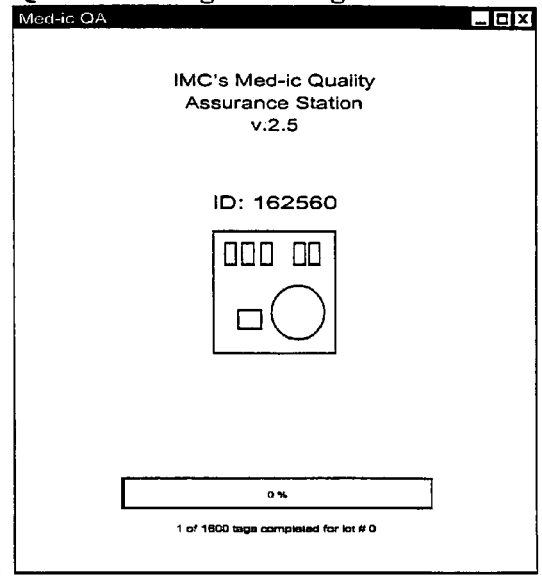
QA2 if the same Tag is scanned twice
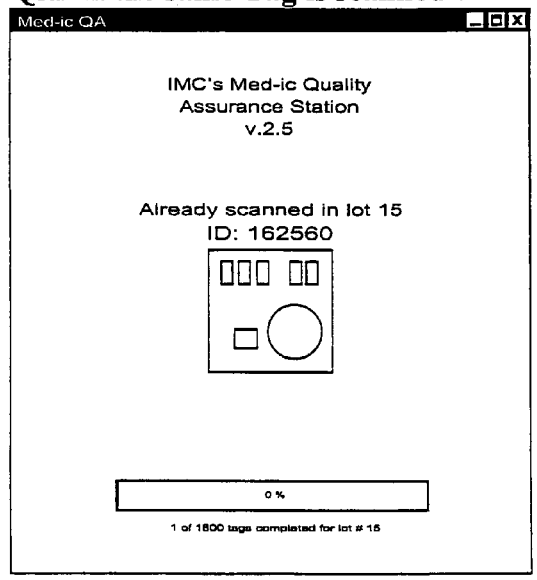
QA2 after entire lot was scanned
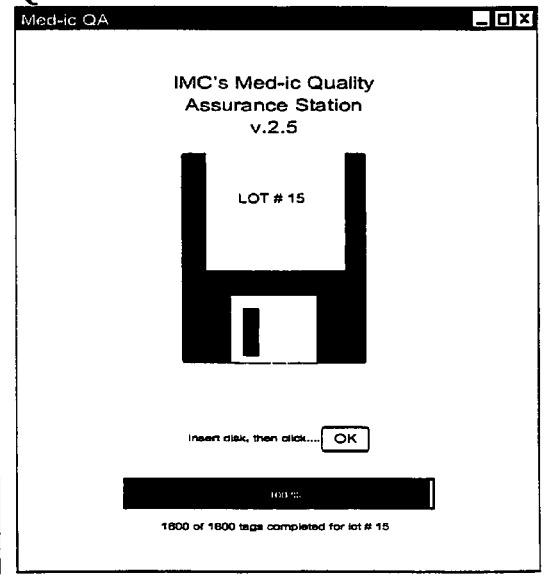
FIG. 8.2: Screenshots of QA2 software

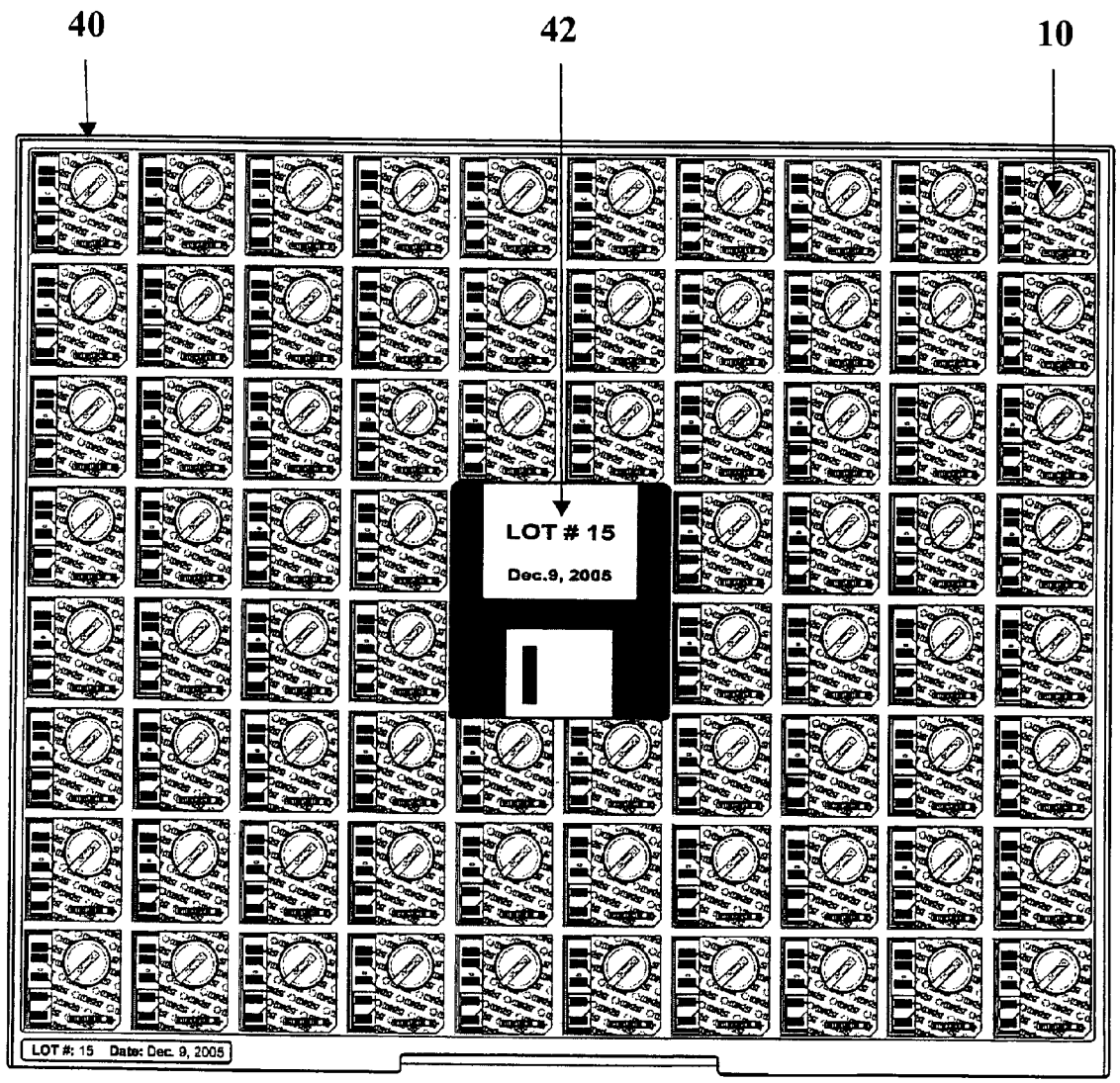
FIG. 9.1

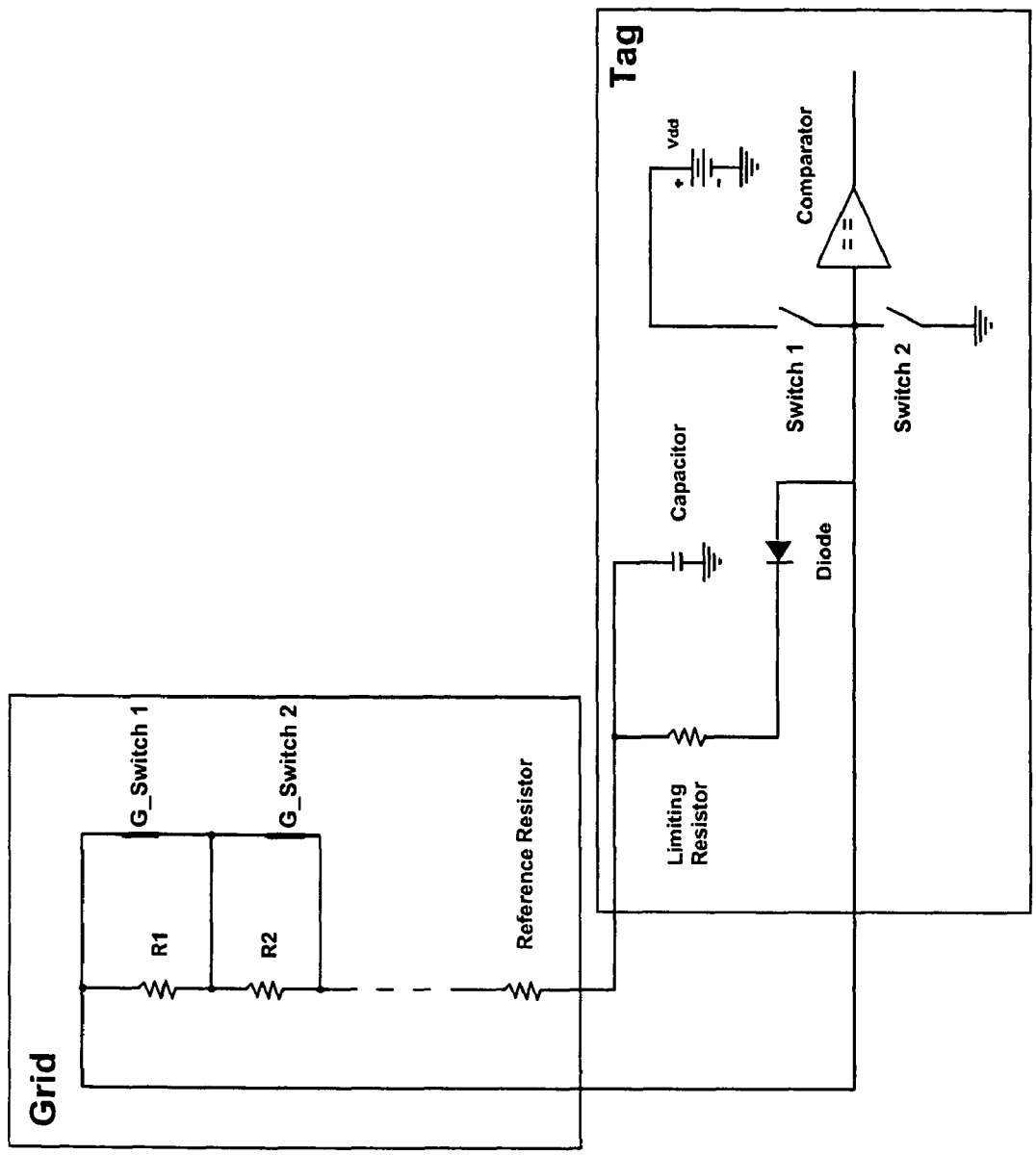
FIG. B1

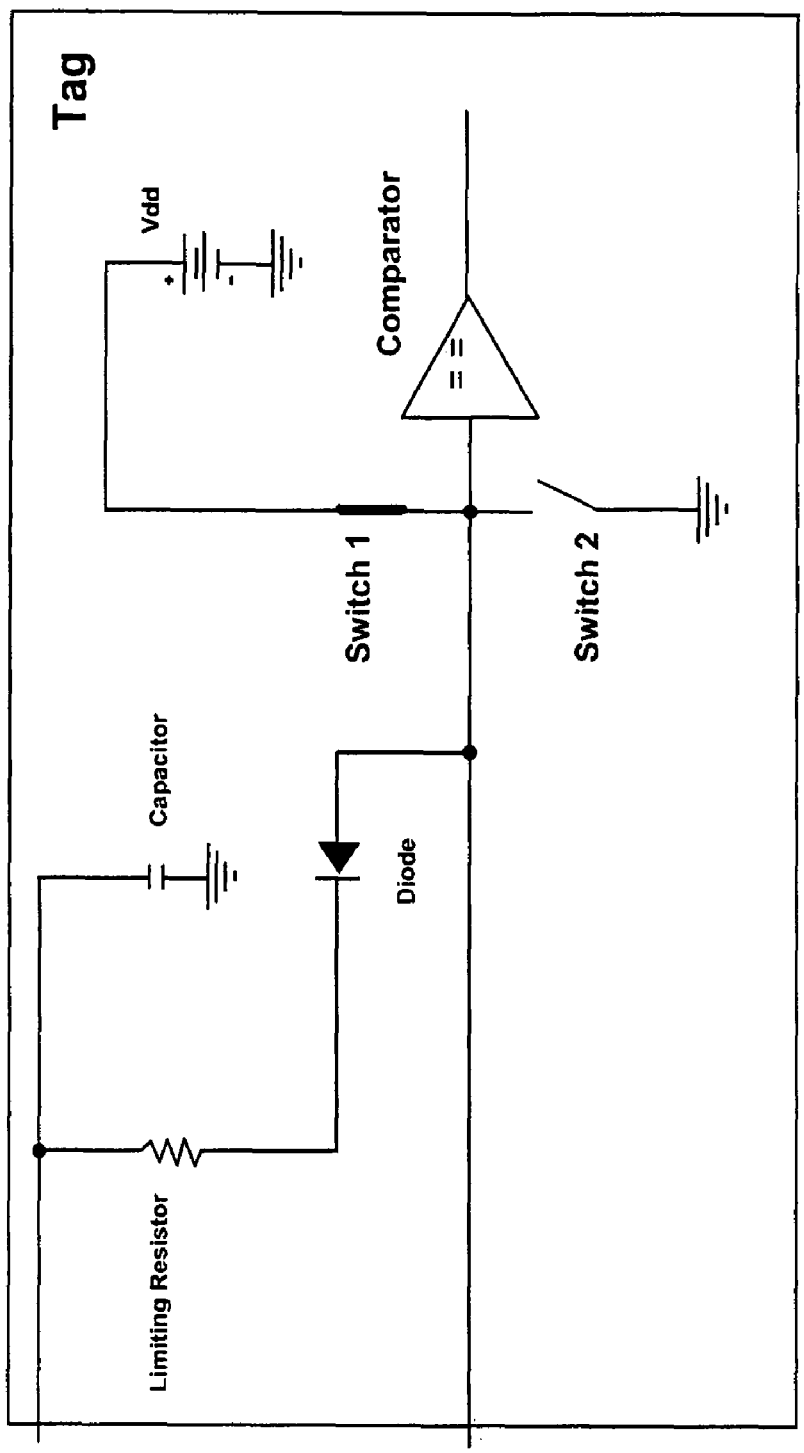
FIG. B2

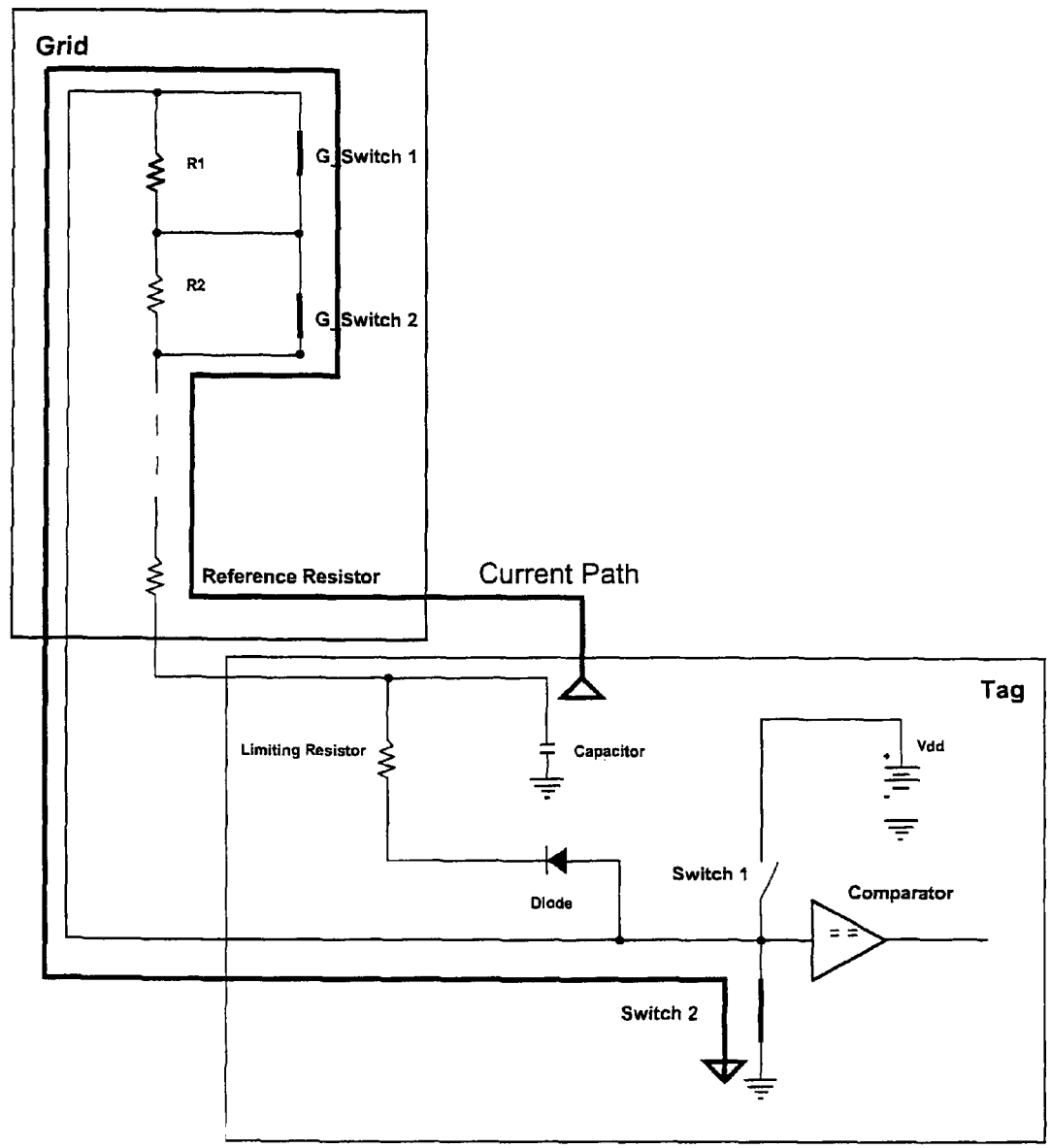
FIG. B3

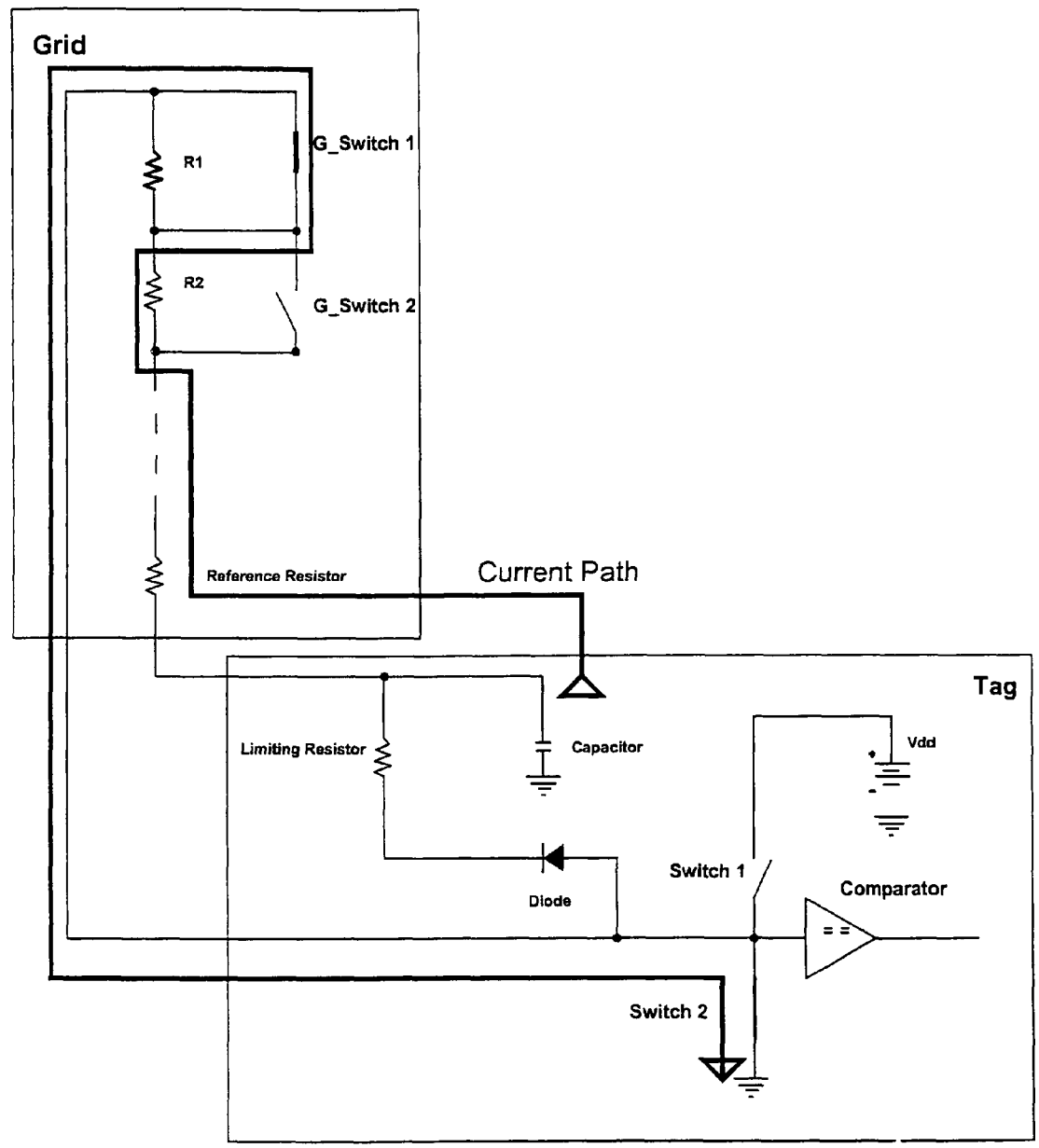
FIG. B4

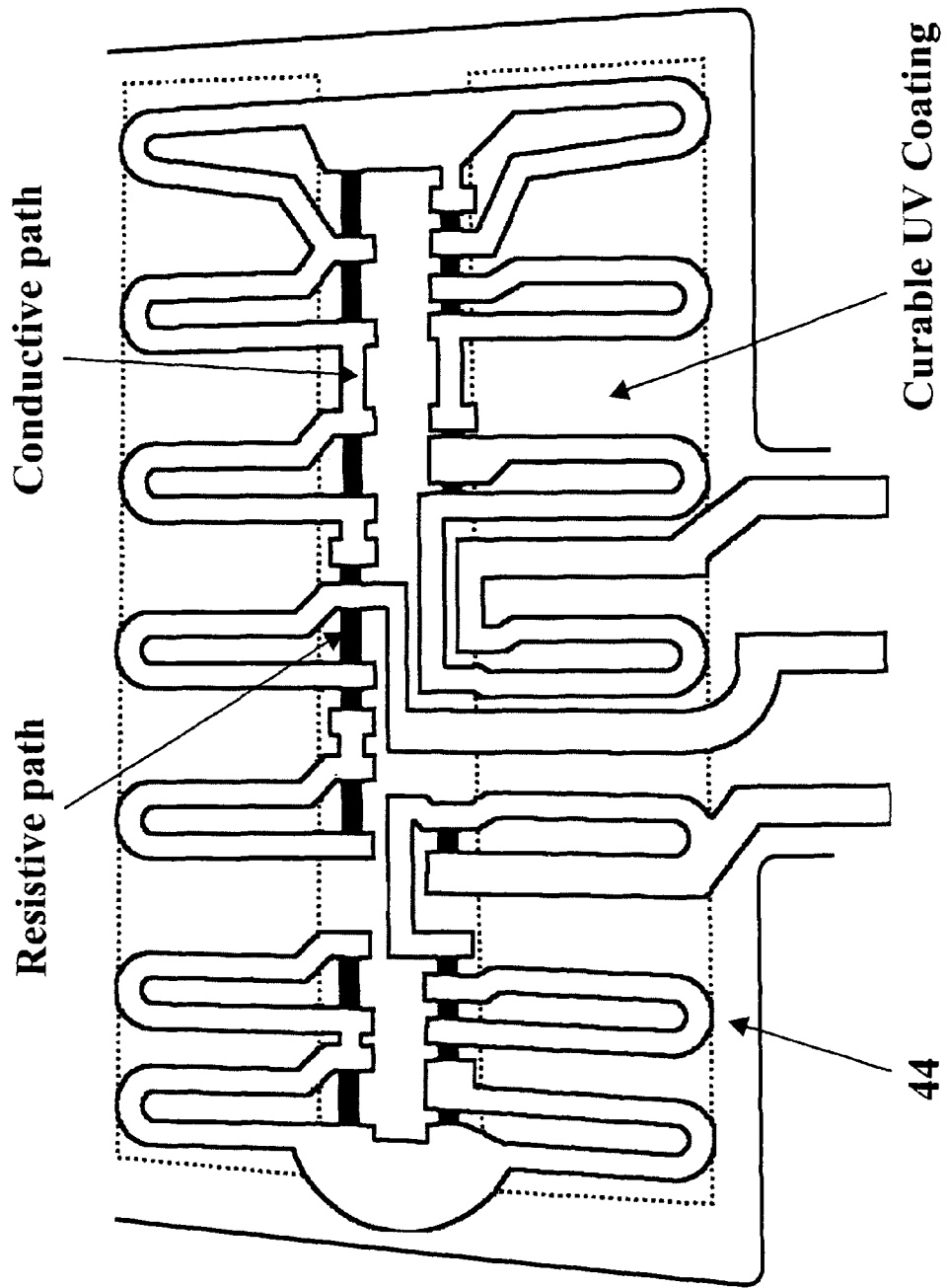
FIG. 10.1

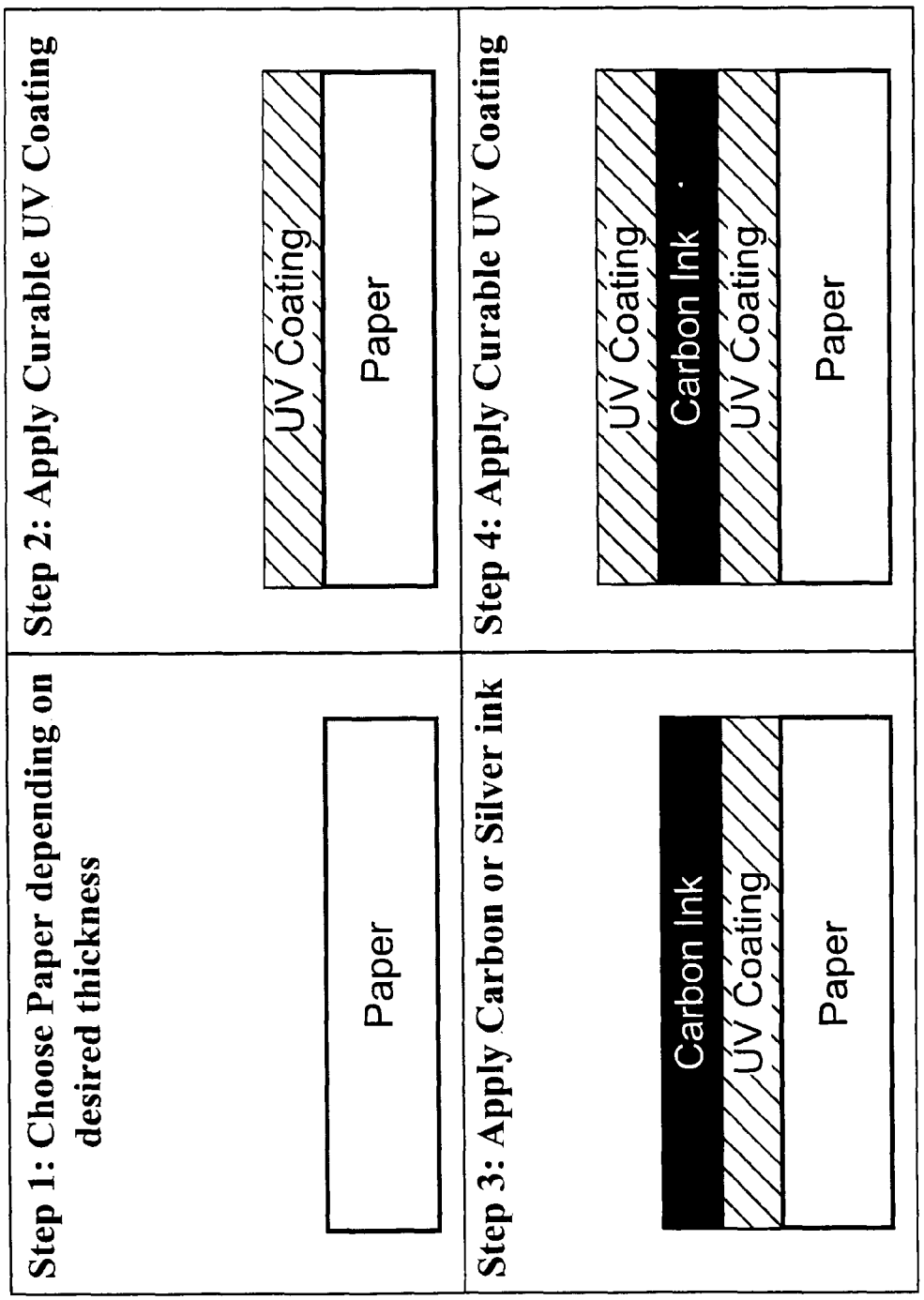
FIG. 10.2

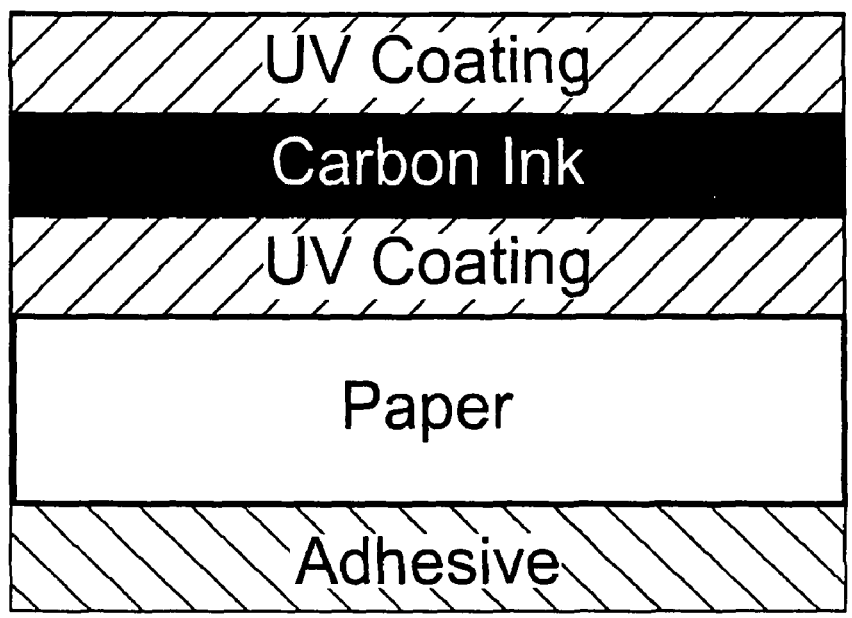
FIG. 10.3

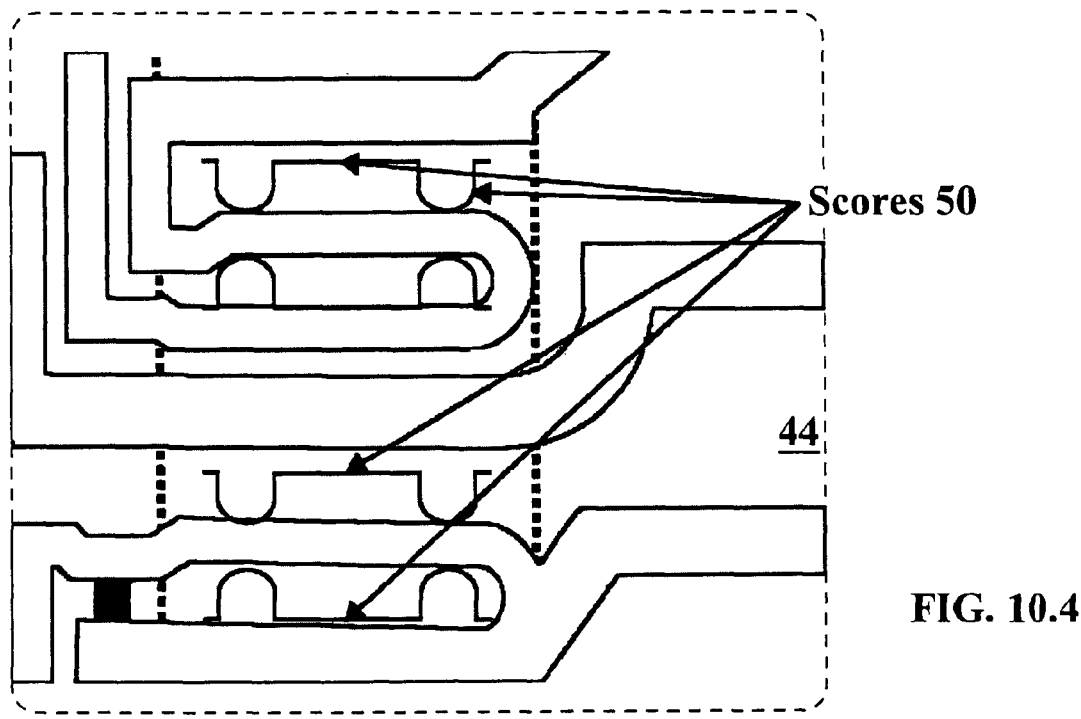
FIG. 10.4
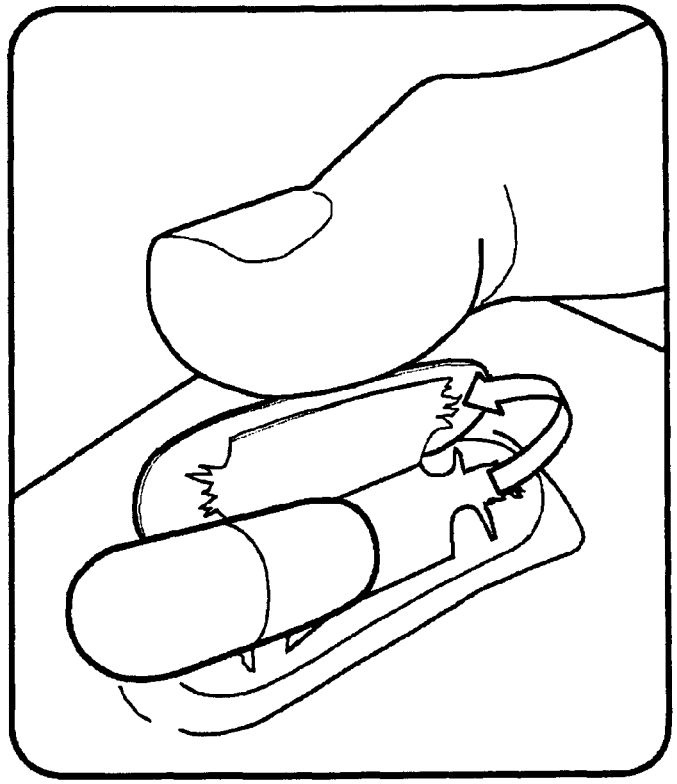
FIG. 10.5

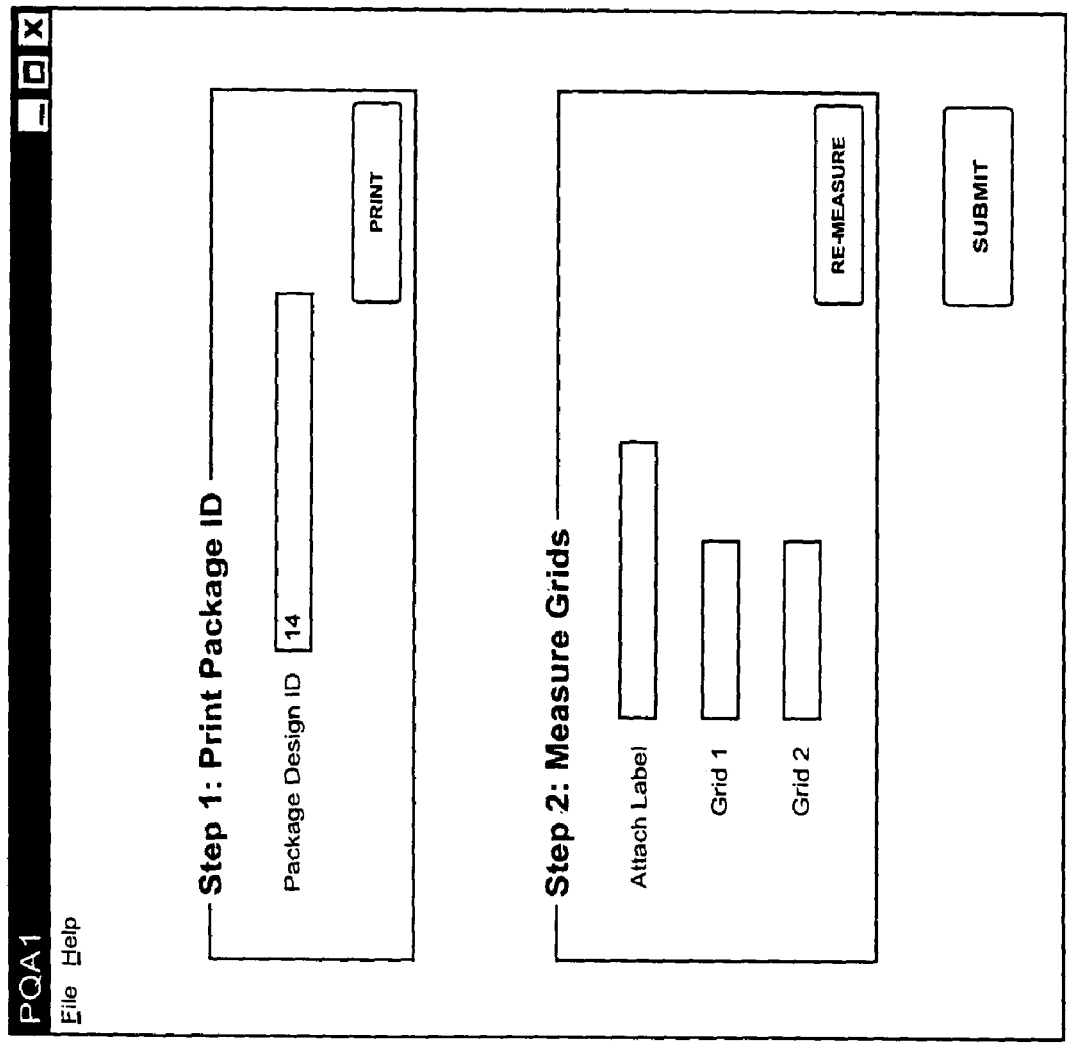
FIG. 11.1

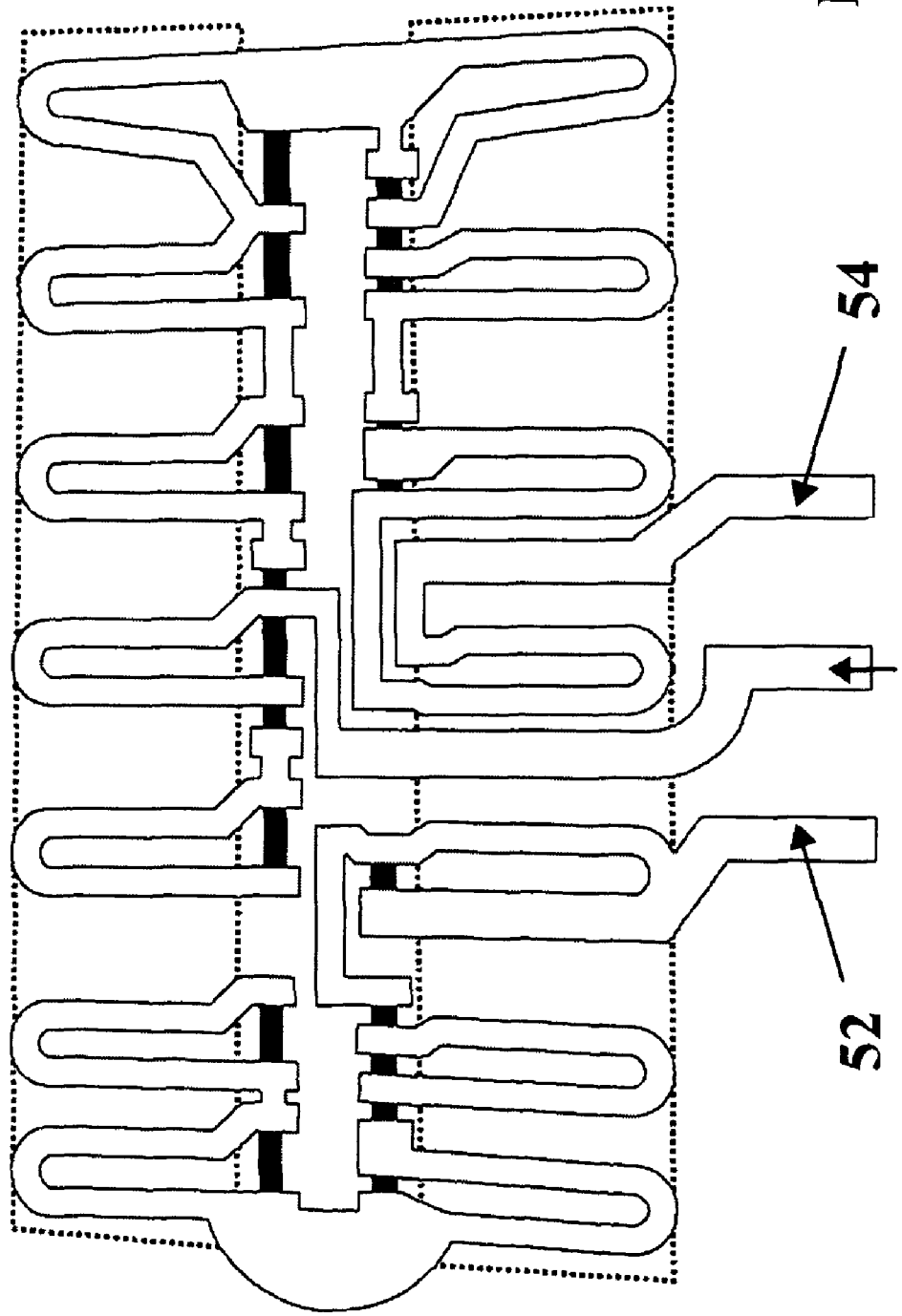
FIG. 11.2

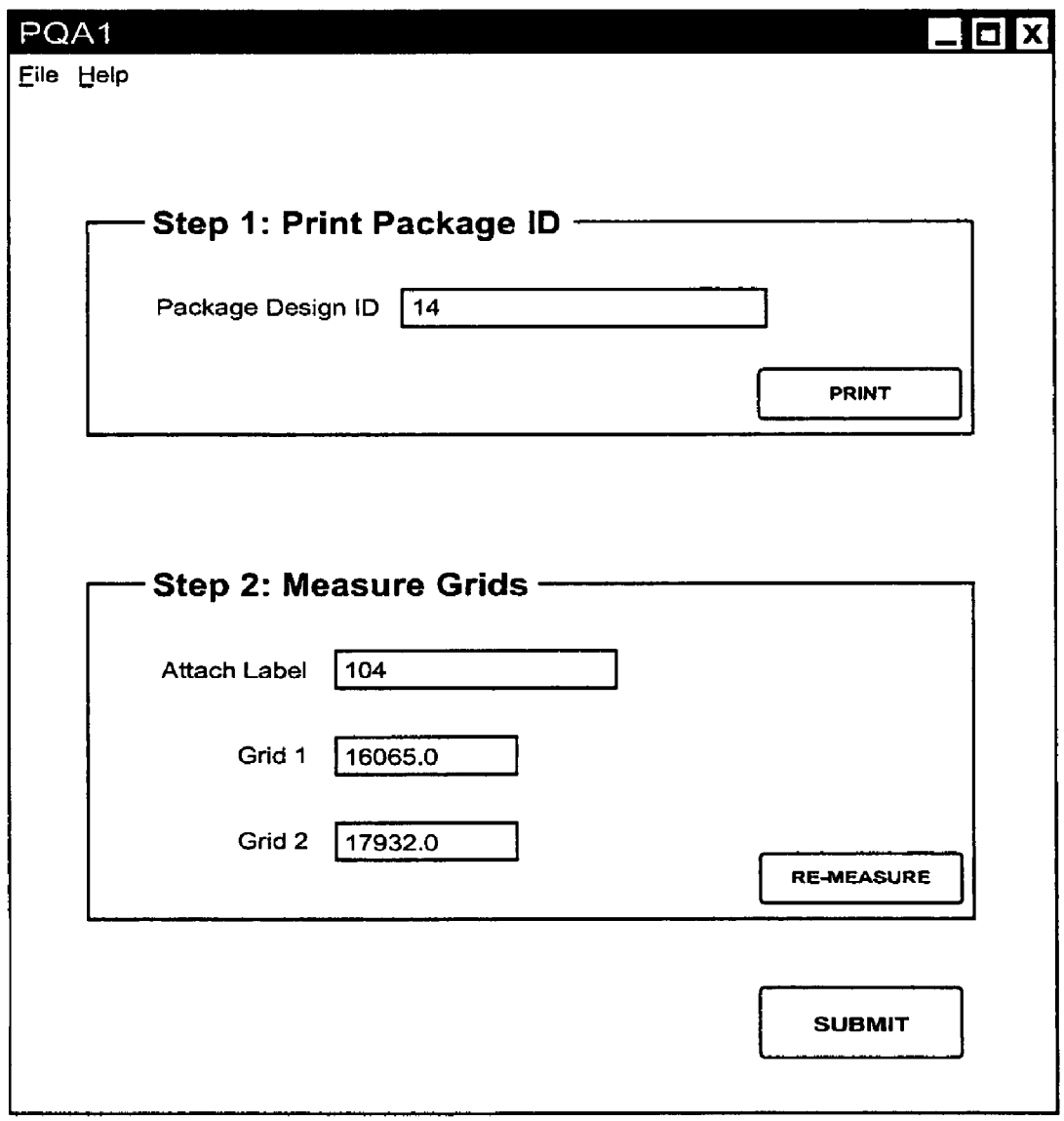
FIG. 11.3

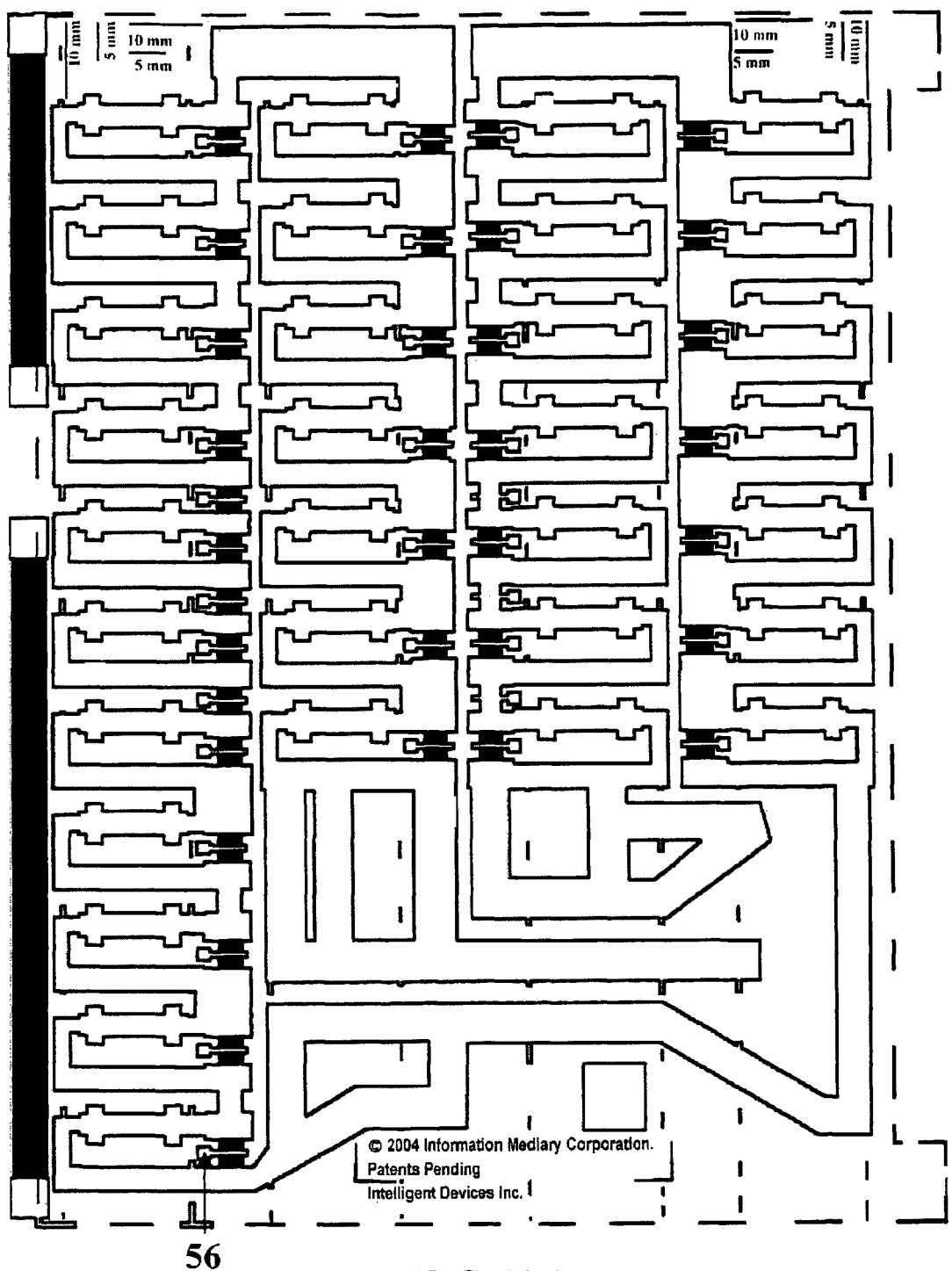
FIG. 11.4

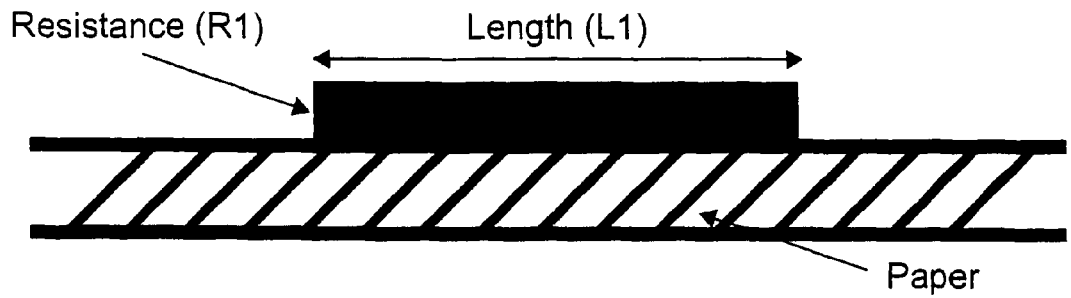
FIG. 11.5
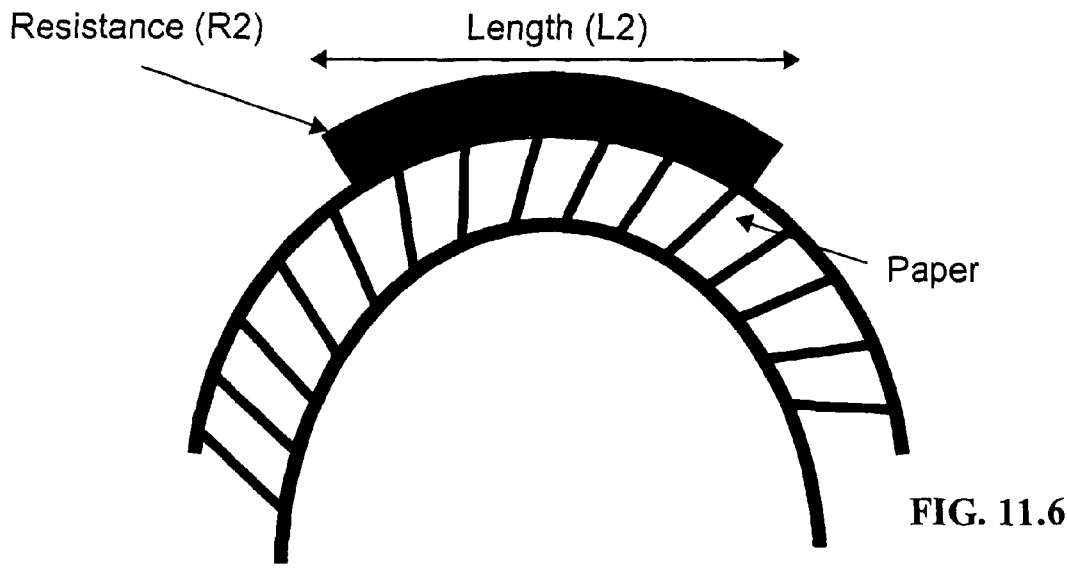
FIG. 11.6
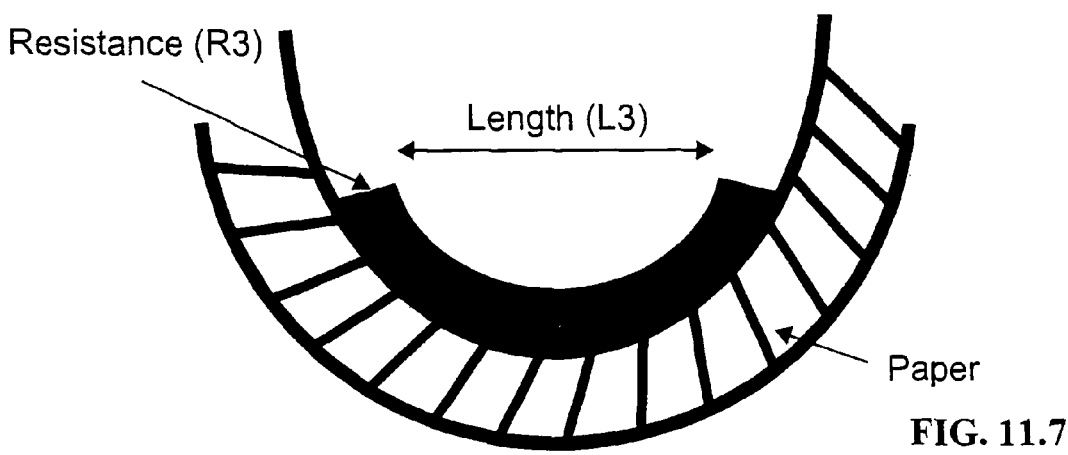
FIG. 11.7

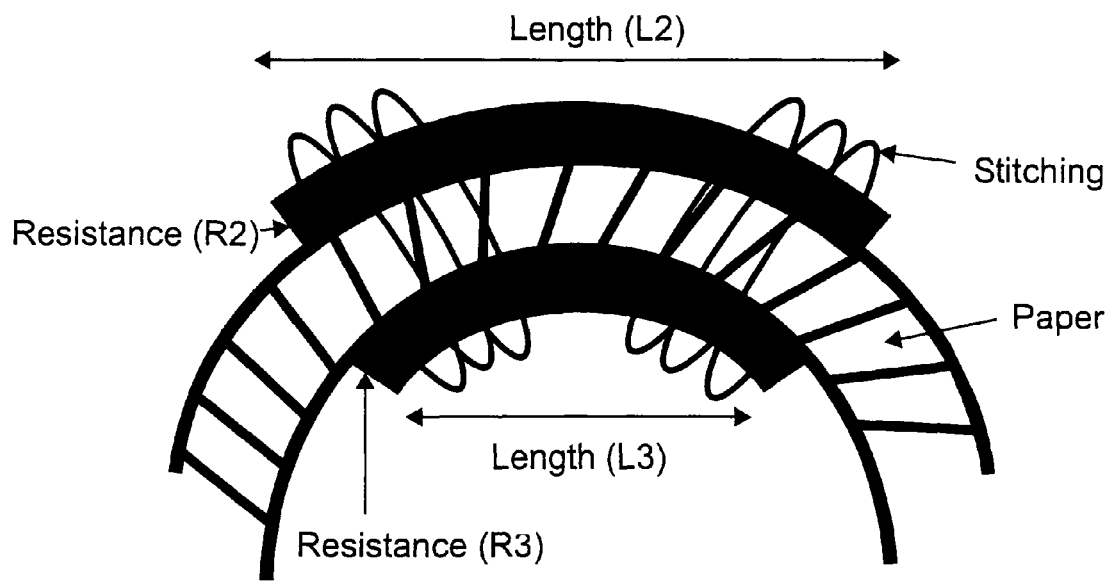
FIG. 11.8
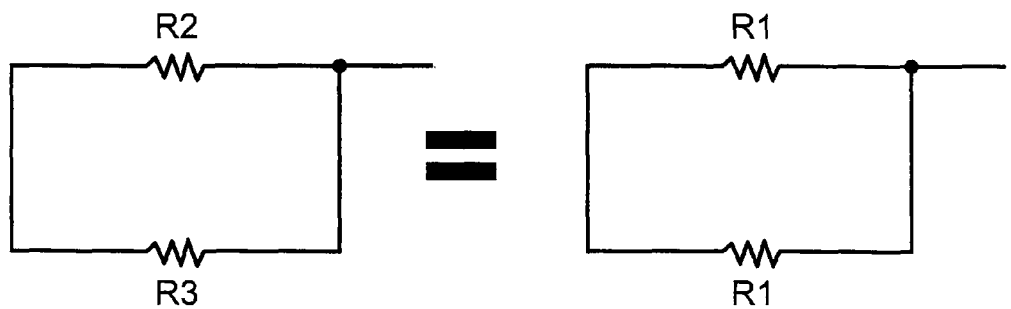
FIG. 11.9

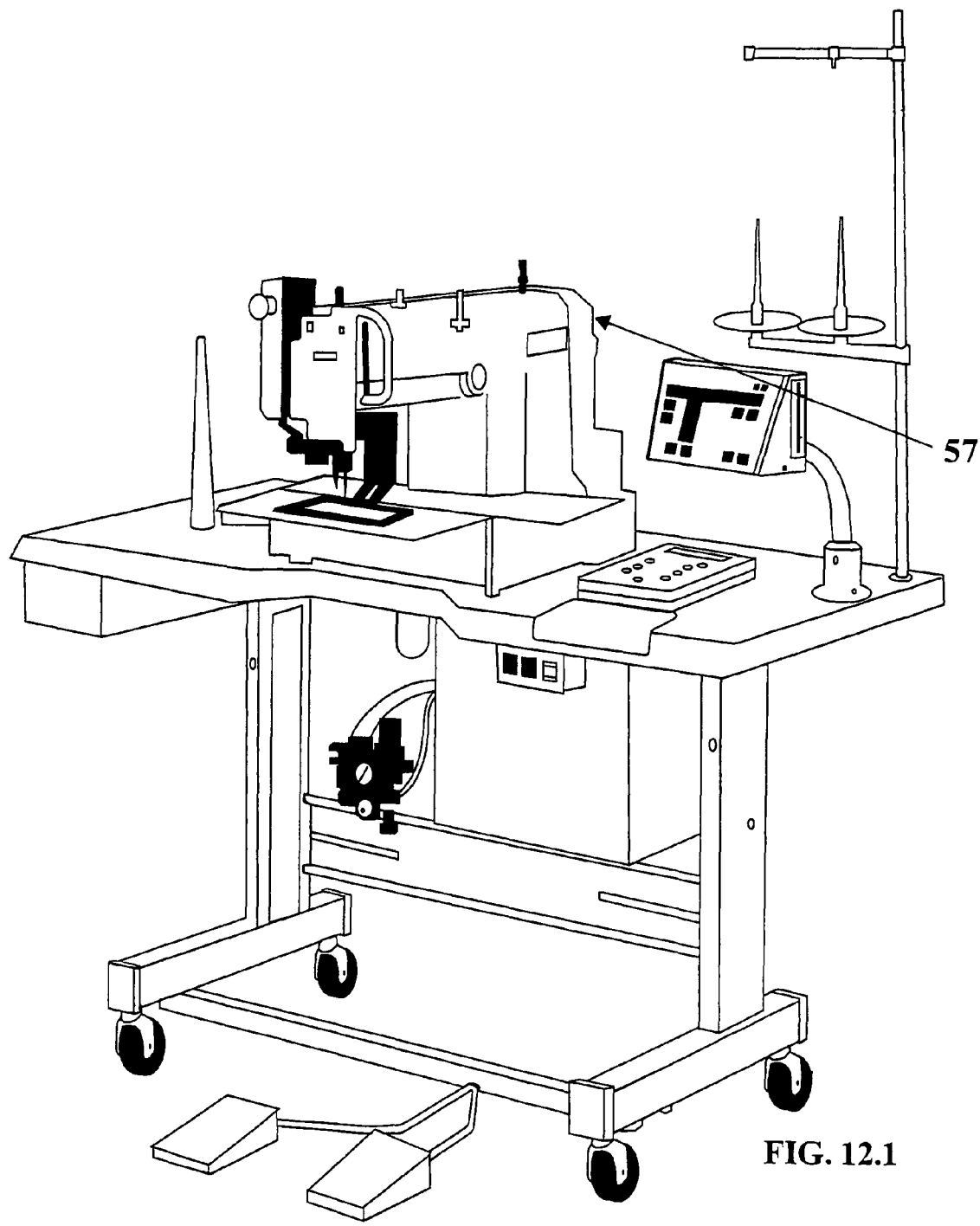
FIG. 12.1

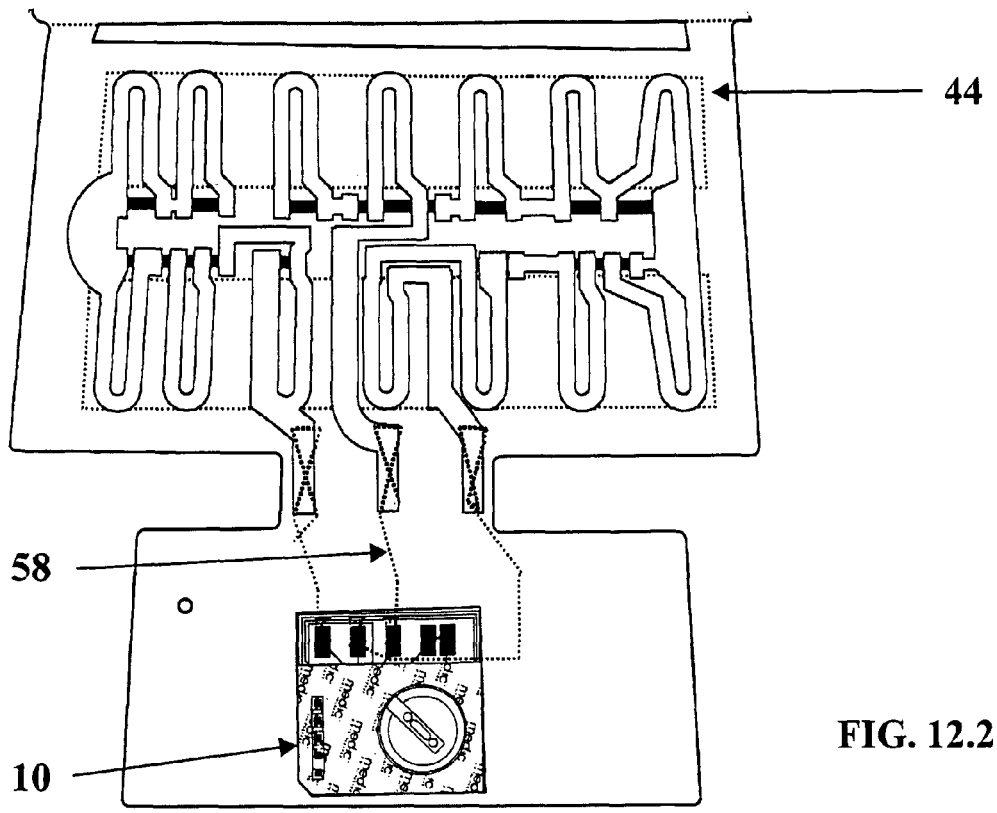
FIG. 12.2 A
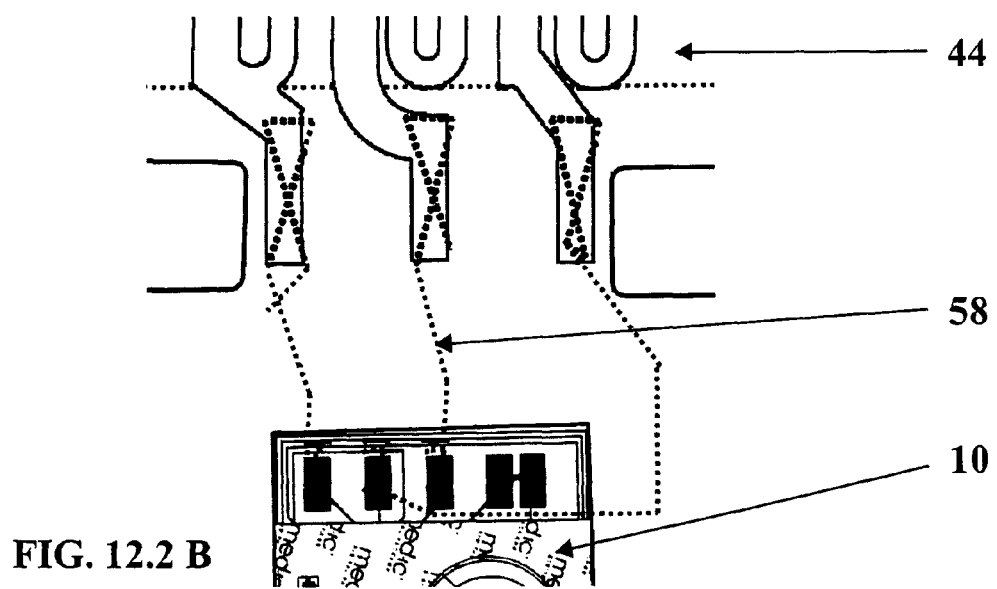
FIG. 12.2 B

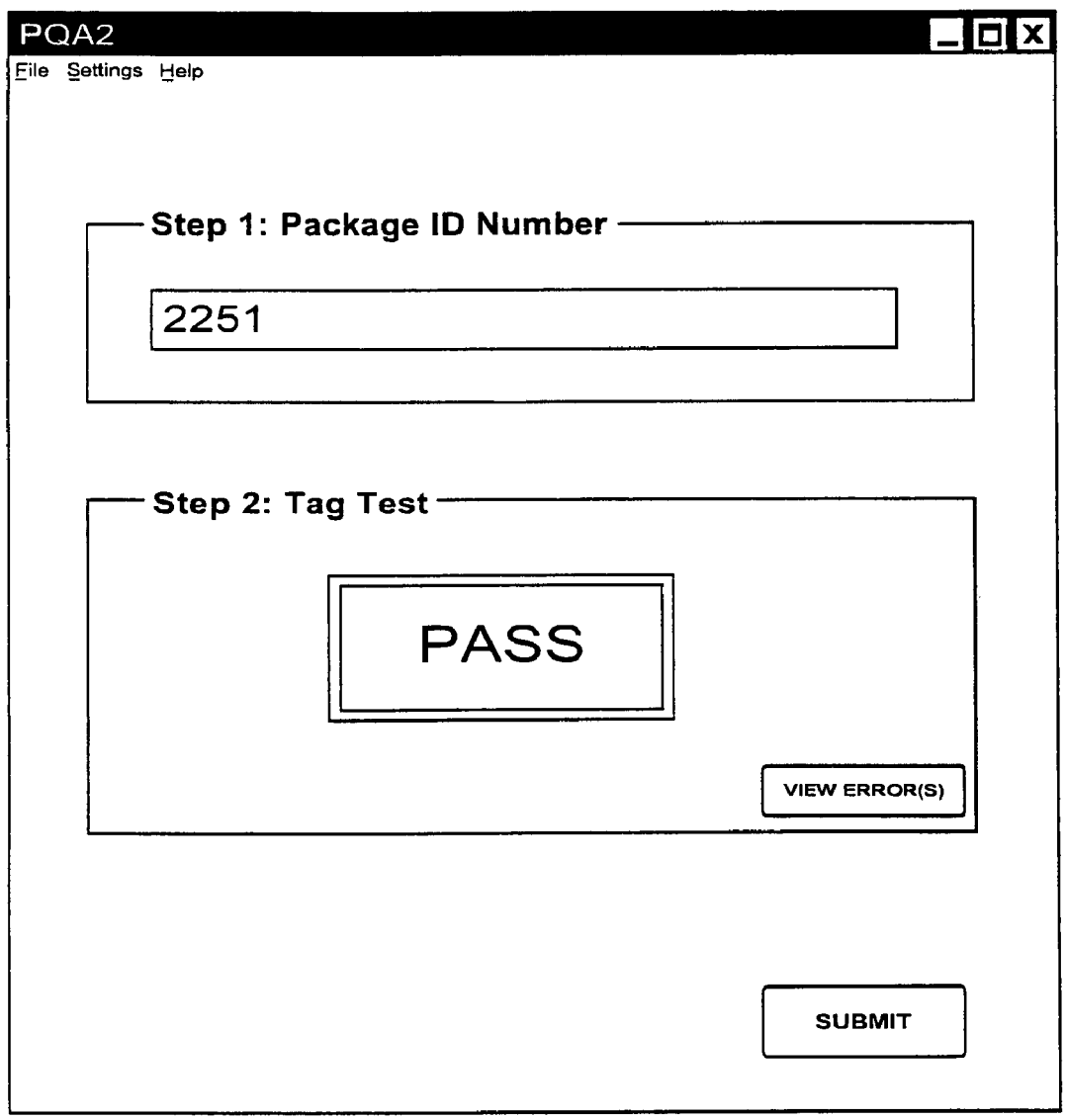
FIG. 13.1

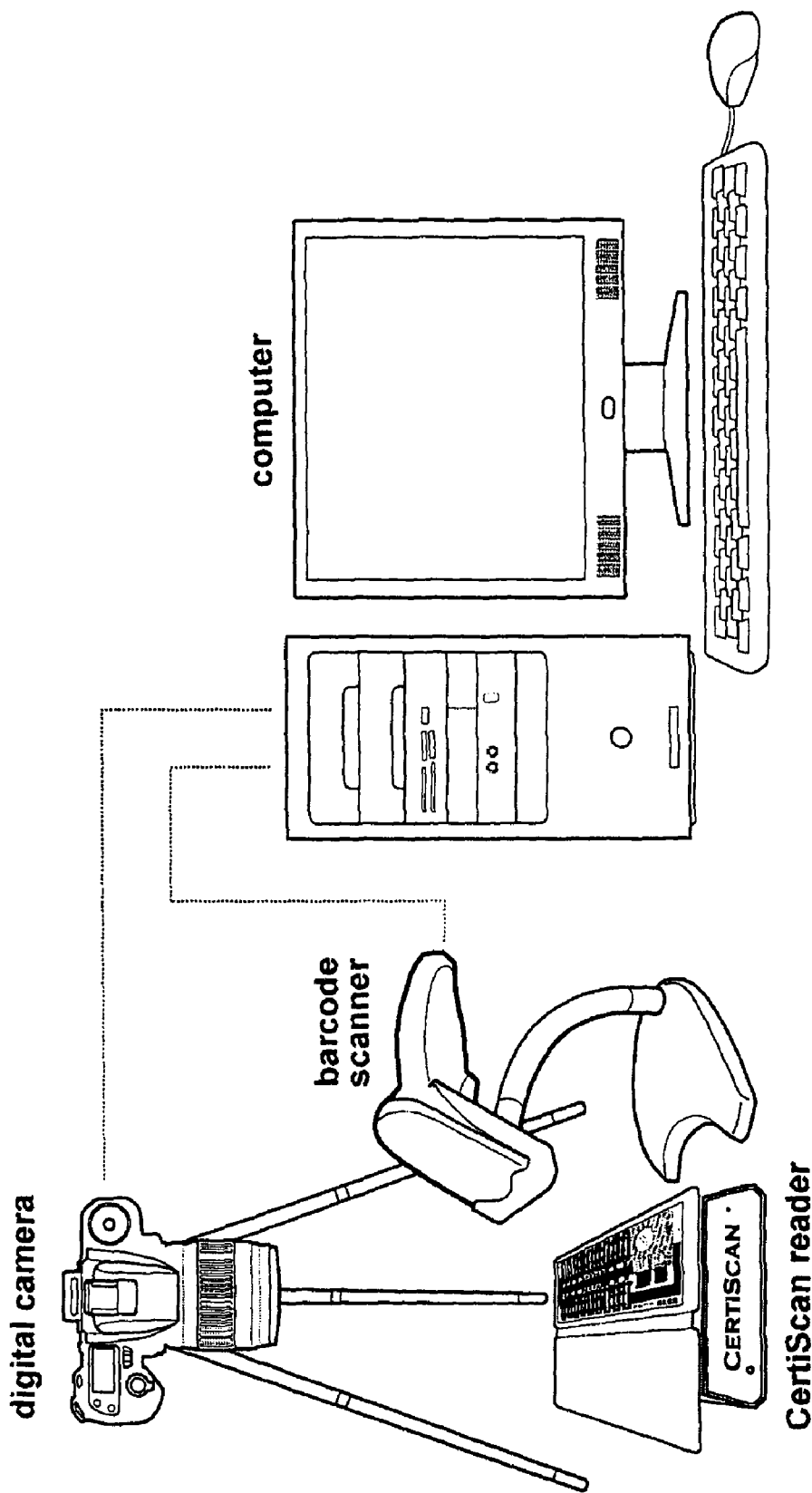
FIG. 13.2

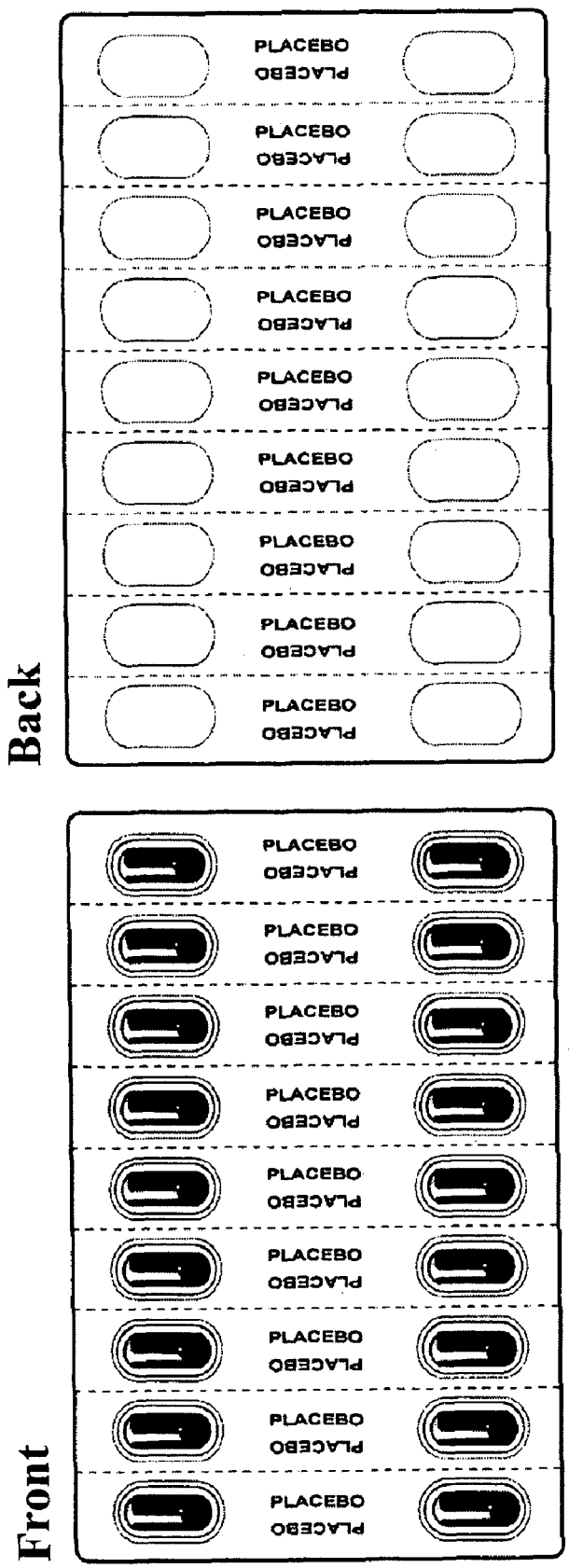
FIG. 14.1

Paper with no blister package
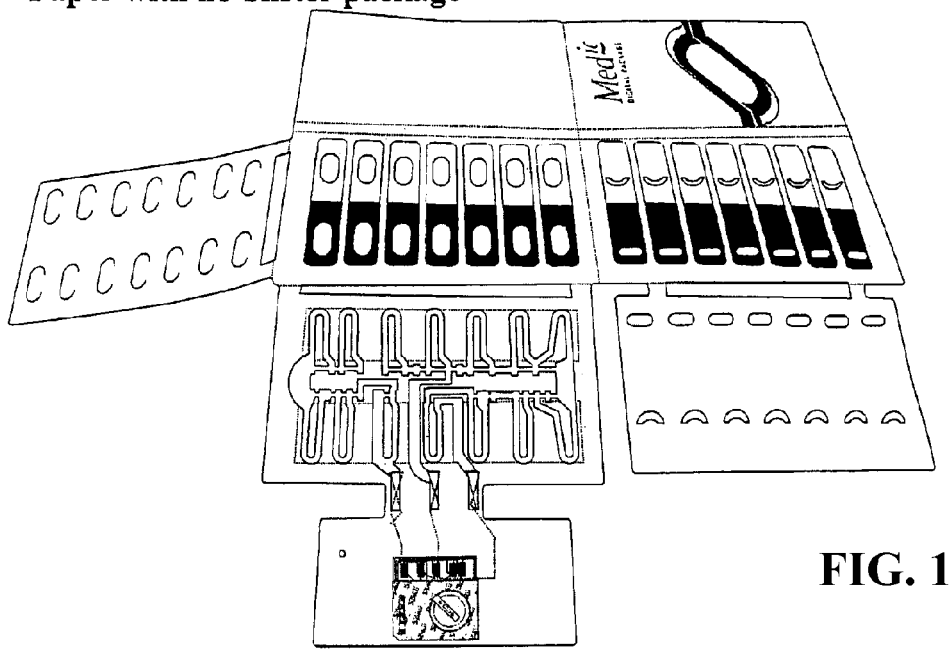
FIG. 14.2A
Paper with blister package in place
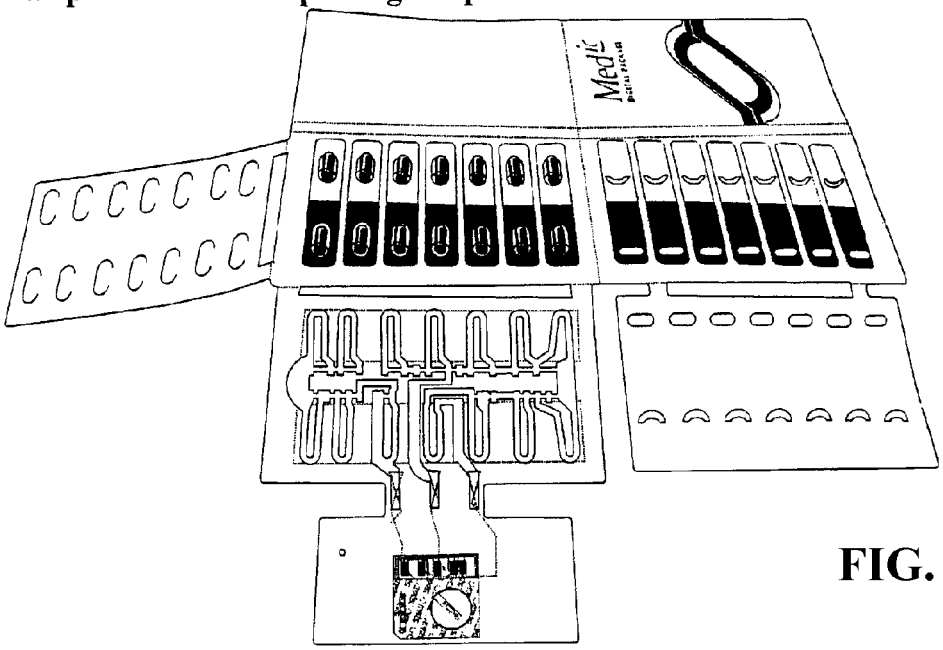
FIG. 14.2B

Step 1: Flip paper containing blister
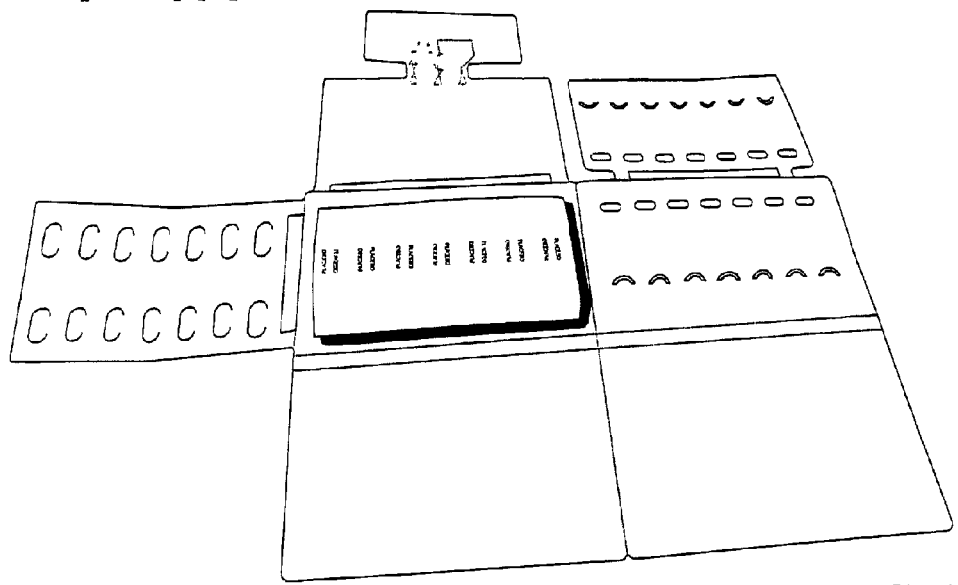
FIG. 14.3A
Step 2: Fold Grid section on top of the blister
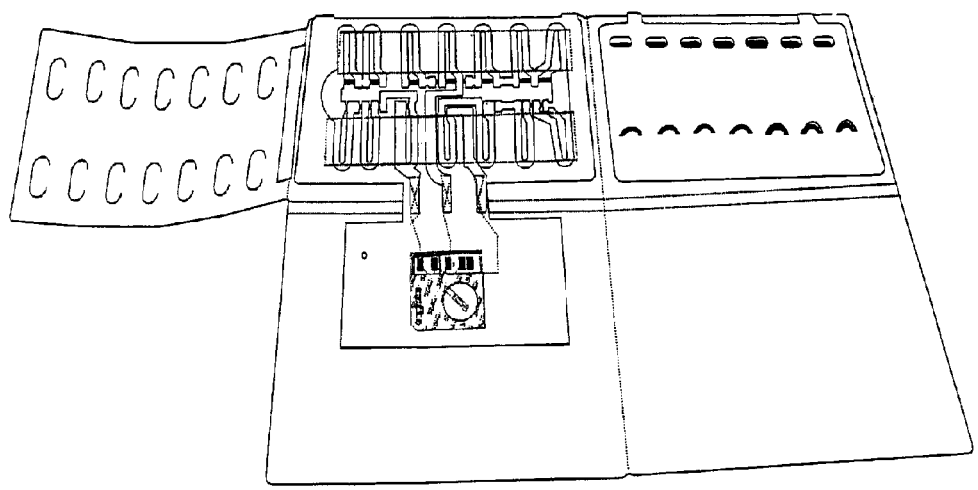
FIG. 14.3B Step 3: Fold left side section on top Grid
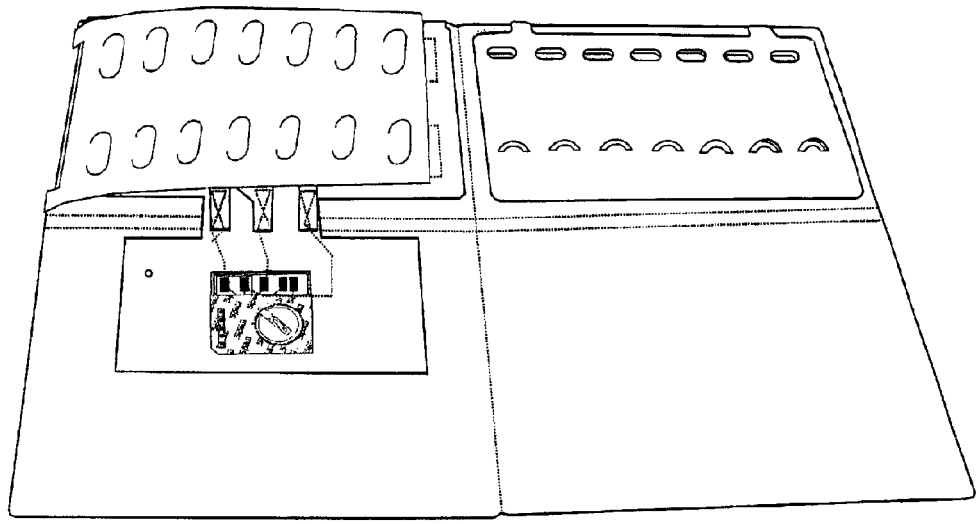
FIG. 14.3C
Step 4: Fold right side of paper on top of the left side
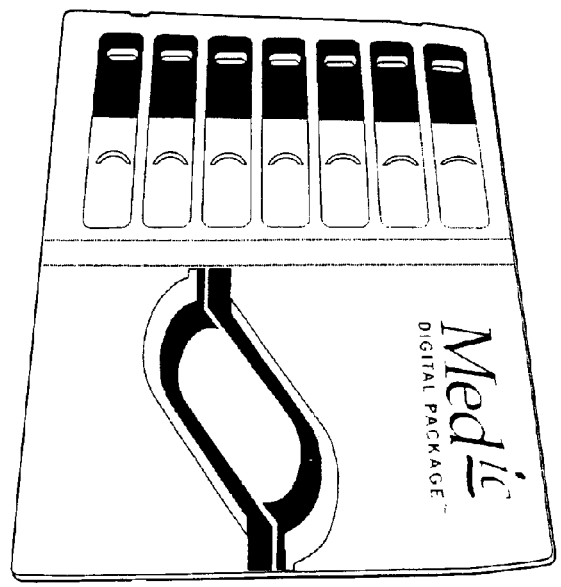
FIG. 14.3D Step 5: Flip paper folded in step 4
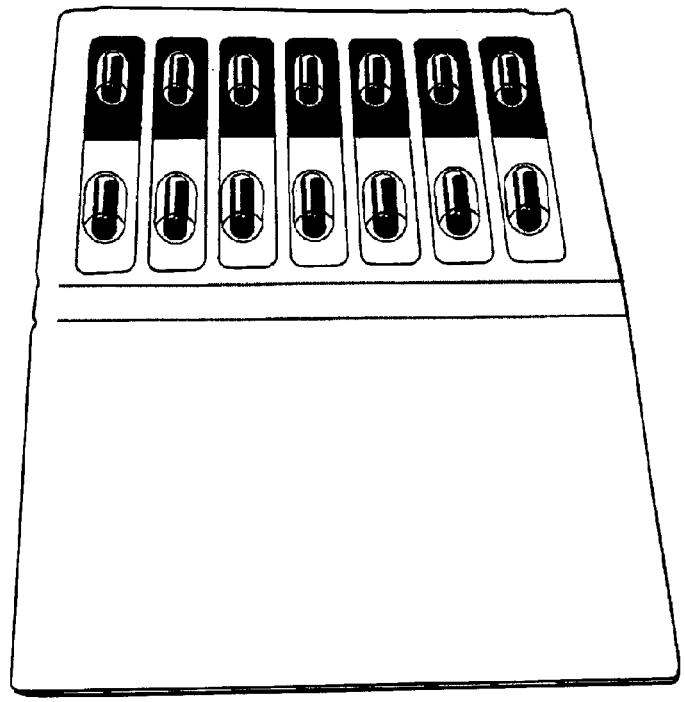
FIG. 14.3E
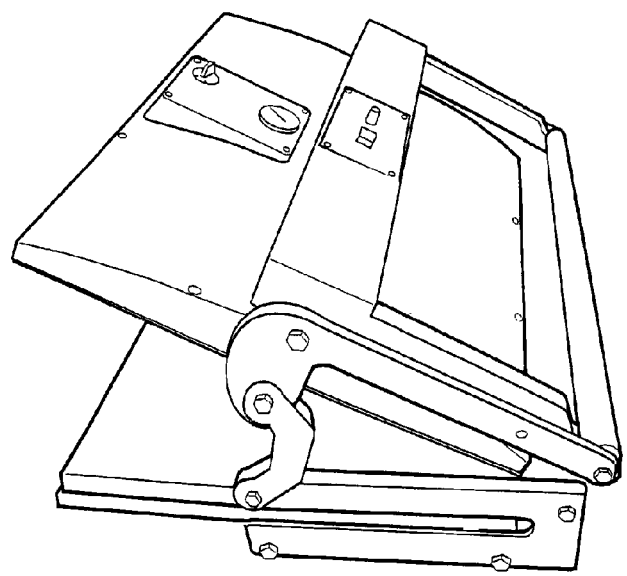
FIG. 15.1 ly as required. Such blister packages are well known. The Med-ic™ ECM tag takes the blister package art a step further in that it provides for electronic traces on the back of the blister package, which traces are ruptured when the contents of the housing pass through the backing sheet. Since the traces are connected electrically to an integrated chip carried by the blister package, information resulting from the rupturing of a trace is available for utilization. In particular, the time and location of the rupturing of a trace can be recorded on the chip for later interpretation by an interested party, such as a physician or a researcher who wishes to determine the time that a pill was taken. This can be very important if the patient is involved in clinical studies or if a tight regimen of medication is required for the treatment of a particular illness. The information accumulated in the chip is downloadable either electronically through connection to a reader, or wirelessly through an appropriate transmitter included as part of the chip.

METHOD FOR MANUFACTURING A CONDUCTIVE GRID FOR ATTACHMENT TO A BLISTER PACKAGE

This application is a continuation of international patent application PCT/CA2006/00074 filed Jan. 20, 2006 and claims the benefit of Canadian Patent Application Serial Number 2,493,410 filed Jan. 20, 2005.

The present invention relates to the steps involved in the assembly, production and quality assurance processes respecting electronic compliance monitor (ECM) tags, and in particular respecting Med-ic™ tags of Information Mediary Corporation.

BACKGROUND OF THE INVENTION

Med-ic™ electronic compliance monitor (ECM) tags are utilized primarily in the pharmaceutical industry in close association with blister packaging of medical items, such as pills or capsules. The pills or capsules are retaining within individual housings of a blister pack, the housings also including a frangible backing sheet through which the pills can be pushed individual There are many other details associated with the above-discussed concept, many of which are set forth in other patent applications of the applicant herein. However, it is also important that the various components associated with the Med-ic™ ECM tag be manufactured to a high degree of tolerance, quality and performance. The steps involved in the manufacture of such tags are detailed herein.

SUMMARY OF THE INVENTION

Broadly speaking the present invention may be considered as providing a method for manufacturing blister packages provided with one or more conductive grids on a surface thereof such that expulsion of an article from a blister will rupture a conductive trace included as a component of said grid, comprising the steps of: preparing an electronic tag having at least microcontroller means, capacitor means, oscillator means, resistor means and diode means thereon; transferring tag identification information to the microcontroller means; installing battery power means to the tag for providing electrical power to the microcontroller means; verifying the integrity of the tag and the components carried thereby; printing a predetermined pattern of conductive traces on a substrate, the pattern being adapted to place the traces in alignment with the blisters of the blister package; verifying resistance levels associated with the traces to ensure that they are within predetermined limits; permanently connecting a tag to the grid such that defined connection points of the tag are conductively connected to defined portions of the traces; verifying the integrity of the grid including the conductive traces and the tag carried thereby; and connecting a grid to a blister package so that each conductive trace of the grid is in alignment with a selected blister of the package, whereby rupture of a trace associated with a particular blister will provide a signal to the tag, allowing the microcontroller means carried by the tag to record the time of occurrence of the rupture event.

The present invention may also be considered as providing a method for manufacturing a conductive grid for attachment to a blister package such that expulsion of an article from a blister of the package will rupture a conductive trace included as a component of the grid, comprising the steps of: preparing an electronic tag having at least microcontroller means, capacitor means, oscillator means, resistor means and diode means thereon; transferring tag identification information to the microcontroller means; installing battery power means to the tag for providing electrical power to the microcontroller means; verifying the integrity of the tag and the components carried thereby; printing a predetermined pattern of conductive traces on a substrate, the pattern being adapted to place the traces in alignment with the blisters of the blister package; verifying resistance levels associated with the traces to ensure that they are within predetermined limits; permanently connecting a tag to the grid such that defined connection points of the tag are conductively connected to defined portions of the traces; verifying the integrity of the grid including the conductive traces and the tag carried thereby; and making the grid available for assembly to a blister package.

BRIEF DESCRIPTION OF THE DRAWINGS

FIG. 1.1 shows a sheet of printed circuit boards (PCB's) of the present invention.

FIG. 2.1 shows an enlarged view of a PCB.

FIG. 3.1 shows apparatus for writing programming information to the PCB's.

FIG. 3.2 shows a schematic representation of the writing process.

FIG. 3.3 shows a screen shot taken during the writing process.

FIG. 3.4 shows a screen shot with a failed PCB identified thereon.

FIG. 4.1 shows a PCB with a battery installed thereon.

FIGS. 5.1A and B show a foam covering for the PCB's.

FIG. 6.1 shows a PCB with foam coverings front and rear.

FIG. 7.1 shows a sheet of PCB's after separation into individual PCB's.

FIGS. 8.1A and 8.1B show the step of checking the integrity of an individual PCB.

FIG. 8.2 shows screen shots taken during the check of FIG. 8.1.

FIG. 9.1 shows a batch of PCB's ready for shipping.

FIG. B1 shows the electrical circuit of a tag in relation to a printed sensor grid (PSG).

FIG. B2 shows the operation of charging a capacitor.

FIG. B3 shows the path taken by the current discharged from the capacitor.

FIG. B4 shows the current path when switch G_Switch 2 is opened.

FIG. 10.1 shows an enlarged view of a grid printed on a substrate.

FIG. 10.2 shows the step-by-step application of coatings and inks to the substrate.

FIG. 10.3 shows an enlarged section of the printed and coated grid.

FIG. 10.4 shows score lines cut into the substrate.

FIG. 10.5 demonstrates removal of an article through a grid.

FIG. 11.1 shows a screen shot of a paper type entered into proprietary software.

FIG. 11.2 shows where a multimeter would be connected to a two-part grid.

FIG. 11.3 shows a screen shot with acceptable resistance readings.

FIG. 11.4 shows a 32-dose grid.

FIG. 11.5 shows a resistor printed on paper, in cross-section.

FIG. 11.6 shows the effect of bending the paper to a convex condition.

FIG. 11.7 shows the effect of bending the paper to a concave condition.

FIG. 11.8 shows resistors printed on both surfaces of the paper.

FIG. 11.9 shows the equivalent circuit to the configuration of FIG. 11.8.

FIG. 12.1 shows a sewing machine used for stitching a tag to a grid.

FIGS. 12.2A and 12.2B show a tag stitched to a grid, with an enlarged view adjacent.

FIG. 12.3 is illustrative of time calculations by the tag.

FIG. 13.1 is a screen shot of an acceptable stitched tag and grid assembly.

FIG. 13.2 show a quality assurance workstation.

FIG. 14.1 shows the front and back of a 14-dose blister package.

FIGS. 14.2A and 14.2B show a 14-dose tag and grid assembly with and without a blister package inserted.

FIG. 14.3A through 14.3E show the steps of folding the blister package into a compact shape.

FIG. 15.1 shows a heat sealing machine used during assembly of a tag and grid assembly to a blister package.

DESCRIPTION OF THE PREFERRED EMBODIMENT

Each step in the production of a Med-ic™ ECM Tag is explained in detail. The steps are explained in chronological order and with particular reference to the drawings and representations appended hereto.

Step 1: PCB Printing

Printed Circuit Boards (PCB's) 10 are printed on a sheet 12 of suitable flexible substrate in 5-inch×4-inch format. FIG. 1.1 shows a sheet of such PCB's.

The holes 14 positioned around the periphery of each PCB are used to align the PCB in an automatic soldering machine used to install electronic components on the PCB.

Step 2: Soldering Components on the PCB

Electronic components are installed on the PCB 10 using an automated soldering machine. The sheet 12 of PCB's (FIG. 1.1) is placed on the soldering machine's customized jig. The jig has protrusions on its surface that engage the holes 14 and thus permit the sheet of PCB's to be located precisely therein. Once the sheet is in place, the components are soldered to the PCB. FIG. 2.1 shows components positioned on a PCB. The components may include a capacitors 16, 18 an oscillator 20, a resistor 22, a diode, 24 and a microcontroller 26.

Step 3: Transferring Firmware to the PCB's

Firmware is software specifically designed to control microcontroller operations. Firmware is saved in individual files and uploaded to a particular website. Each file contains a Tag Firmware Version and a unique Tag Identification (ID) Number. These files are downloaded to a Personal Computer (PC) connected to a Wouter Box 28.

The Wouter Box 28 is a specialized piece of hardware that allows 20 PCB's to be programmed and serialized simultaneously. FIG. 3.1 shows a Wouter Box 28. The Wouter Box 28 is connected to a Nail Bed 30 comprising 100 pins to allow the 20 PCB's carried by a sheet 12 to be programmed simultaneously. The Nail Bed 30 enables simultaneous transfer of 20 firmware files from a Wouter Box 28 to 20 PCBs. A Nail Bed is shown in FIG. 3.2 which schematically illustrates the process of transferring firmware from a PC to a Wouter Box to a Nail Bed to 20 Med-ic™ ECM Tags.

To control the transfer of firmware, "Big Burner", also known as QA1 software, is used. Big Burner software is installed on a PC connected to Wouter Box 28. FIG. 3.3 shows the screenshot of Big Burner software.

In addition to transferring firmware, Big Burner also verifies that the oscillator calibration coefficient is not corrupted due to poor contact between the Nail Bed pins and the PCB's. Big Burner automatically marks any PCB's that were not successfully programmed with the firmware, so that these tags can be removed from the assembly process. FIG. 3.4 shows a screenshot of Big Burner displaying a failed attempt at programming one of 20 PCBs. The failed attempt is shown with a large "X" at position number 4 in the bottom line of PCB's.

Step 4: Battery Installation on the PCBs

Once the PCB's are programmed, a 3.3-volt battery 32 is installed on each PCB by soldering. FIG. 4.1 shows a PCB with the battery installed thereon.

Step 5: Protective Foam Placement on the PCBs

A layer 34 of protective foam is applied to the PCB's. Since both sides of the foam are adhesive, the foam is adhered to the PCB's. The front side of the foam identifies the PCB type (i.e., Med-ic™) and the Firmware Version. The backside of the foam has a protective paper layer attached. When adhering the foam 34 to the PCB's, this paper is first peeled off to expose the adhesive. The backside of the foam is then attached to the PCB's. FIG. 5.1A and B show the front of the foam and a single PCB with foam attached.

Step 6: Foam Placement on the PCBs

Another layer 36 adhesive foam is glued to the back of the PCB's. This allows the option of attaching PCB's to any paper material. Paper from one side of the foam 36 is peeled off and that side is attached to the back of the PCB. The other side of the foam is left with its protective backing in place. When the PCB is to be affixed onto a paper material the protective backing is removed and the PCB attached. FIG. 6.1 shows the front and back of the foam.

Step 7: PCB Sheet Separation

A sheet 12 of PCB's 10 is cut into 20 separate PCB's. These PCB's 10 are now known as Tags, and will continue to be identified by the reference number 10. FIG. 7.1 shows the individual tags 10 separated from each other.

Battery Life Measurement:

To assure the quality of the batteries attached to the Tags, battery life is now measured.

The rate of loss of energy from batteries is often irregular, making it difficult to measure and predict. Factors such as quality, lithium content, connections of anode and cathode, and condition of the separator and electrolyte system can contribute to inconsistency in energy depletion.

Special firmware, "Battery Test Firmware", has been developed to monitor the energy and voltage level of a battery through its entire life. Battery Test Firmware checks and records the energy and voltage level of a battery at regular intervals. Recorded information is displayed when the Tag is scanned on an RF reader connected to a PC loaded with the Battery Test Firmware.

Tags are randomly chosen from a production batch after they have been completely assembled. These selected Tags are then programmed with the Battery Test Firmware using Big Burner software. A resistor of low tolerance (approximately 0.1%) is connected to each programmed Tag. This resistor serves as a reference unit for the battery voltage measurements. These Tags are stored in a warehouse where they are periodically scanned to view the battery's energy and voltage level history. The functional life of a lithium battery is approximately 2 years.

Step 8: Quality Assurance Check on Each Tag

Each Tag 10 is checked with Quality Assurance 2 (QA2) software. To communicate with the Tag, QA2 software uses the CertiScan™ Reader 38. A Tag 10 is placed on the reader to start communication with the QA2 software. The procedure of placing the Tag on a reader is also referred to as scanning. FIG. 8.1 shows the Certiscan™ Reader 38 and a Tag 10 being scanned.

QA2 checks Timer 1 and battery voltage. Any Tag that fails either of these tests is deemed unacceptable for further use. Tags that pass these checks are assigned unique ID Numbers that are saved to a QA2 floppy disc. In addition, the test results for each Tag are also saved. On completion of this step only successfully programmed and readable tags have passed through the inspection process. FIG. 8.2 shows screenshots of QA2 software.

Step 9: Shipping and Handling

Tags 10 that pass QA2 are placed in a plastic tray 40. A tray 40 is capable of holding 80 Tags and 20 trays form a Lot. (Thus, 1 Lot consists of 1600 Tags). Each Lot also includes a floppy disc 42 containing the ID numbers and QA2 test results for all Tags in that Lot. Three Lots are placed in one Box.

One percent of the Tags are held back for quality testing and are sent to the engineering office. Boxes of tags are shipped to the user.

FIG. 9.1 shows a tray 40 containing 80 Tags and the floppy disc 42 for the Lot to which this Tray belongs.

Description of Steps Involved in Producing a Printed Sensor Grid (PSG) Compatible with a Med-ic™ ECM Tag Having manufactured a large number of tags 10 for the blister package market, it is then necessary to marry each tag to a Printed Sensor Grid (PSG) adapted for each blister package provided with a tag. A PSG will carry the conductive rupturable traces in a particular pattern dependent on the layout of the blister package itself and it will also carry conductive stitching connecting the rupturable traces with the tag 10.

Background Information

A paper production facility designs and manufactures paper or paper label stock to work with Med-ic™ ECM Tags. A PSG is then printed on its surface. The PSG is also known as a Grid 44.

A Grid consists of conductive and resistive paths connected to a Tag 10 by stitching with conductive thread, also the subject of separate patent applications. This puts the Tag 10 and Grid 44 in electrical continuity. Details of connecting a Tag to a Grid are described in Step 12 hereinafter. The connection between the Grid and the Tag enables the Tag to monitor the electrical characteristics of the Grid. The electrical circuit comprised of a connected Tag and Grid is shown in FIG. B1.

Operations of the Circuit

In FIG. B1, components residing on the Tag 10 and the Grid 44 are enclosed in rectangles labelled "Tag" and "Grid". Power is supplied to this circuit by a 3.3 Volt battery (Vdd).

Initially, Switch 1 is closed to allow Vdd to charge the Capacitor. The Limiting Resistor prevents overflow of current to the Capacitor. When the Capacitor is charged to approximately 1.1 Volt, the Comparator records a Value of 1. This indicates that the Capacitor's charged value is higher than the Comparator's threshold value. FIG. B2 shows the operation of charging a Capacitor.

When the Comparator records a Value of 1, a Timer is set to zero. The Capacitor is discharged to Ground through the components of the Grid. Closing Switch 2 allows the Capacitor to discharge to Ground. Current flows first from the Capacitor to a Reference Resistor on the Grid. When the current reaches the point of the Resistors in parallel (FIG. B1 with R2 in parallel with G_Switch 2), it chooses the path of least resistance and passes through the closed G_Switch. After passing through all closed G_Switches, the current goes through closed G_Switch 2 to ground. FIG. B3 shows the path taken by the current discharged from the Capacitor.

A Diode in the circuit prevents the current from flowing through the Limiting Resistor. Therefore current is forced to take the path shown in FIG. B3. The Reference Resistor is three times bigger than any other Resistor in the grid circuit. Since the printing of a grid can vary from grid to grid, the Resistors can also vary. The Reference Resistor provides an average value for a specific Tag to establish a relative current when the Capacitor is discharging.

As soon as the Capacitor begins discharging, a Timer is started to measure the time it takes for the Capacitor to discharge. Once the Capacitor's discharge value reaches the Comparator's threshold value of 1.1 Volts, the Comparator records a Value of 0 and stops the Timer. The time measured by the Timer is stored in the EPROM of the microcontroller.

If G_Switch 2 in the grid is opened, as shown in FIG. B4, the current's path changes. Current now flows through R2, the path of least resistance. The path through R2 increases the time for the Capacitor to reach the threshold value of the Comparator.

The Microcontroller compares the opening and closing times of G_Switch 2. If the times do not match, the Microcontroller decides that G_Switch 2 is open.

Step 10: Printing Sensor Grids

Electronic components such as resistors and conductive traces are printed on the surface of the paper or label stock. Silver ink is used to print conductive traces 46 and carbon ink is used to print resistors 48 (resistive paths). These printed elements are collectively referred to as the Grid.

A Tag and Grid form an electronic circuit that allows the Tag to monitor the Grid for changes in its electrical characteristics. FIG. B1 shows schematically the circuit formed by the Tag and the Grid. The Grid is printed on paper or label stock as shown in FIG. 10.1. This Grid behaves and operates as described under the Background section.

A Flexographic printing process as described in other patent applications is used to print the Grids. FIG. 10.2 illustrates the step-by-step application of coatings and inks to the paper's surface. In lieu of or in addition to coating, protective self-adhered tape may be used.

As described in FIG. 10.2, Step 1 involves choosing the paper thickness. Ten- or 12-point paper is generally used. Alternatively, 3 mil or similar self-adhesive label stock may be used.

In Step 2 a layer of Curable Ultraviolet (UV) Coating is applied to the paper. This coating prevents cracks from forming in the resistive or conductive paths when the paper is bent.

Cracks can interfere with the electrical continuity of the paths causing the system to malfunction.

In addition, paper is composed of fibres, making its surface irregular and sensitive to changes in temperature and humidity. Changes in a paper's surface architecture alter the electrical characteristics of paths printed on it. Curable UV Coating makes the paper's surface more uniform and resistant to temperature and humidity effects.

UV Coating also provides extra flexibility if the paper has a clay coating. Clay coating is applied to paper to make it glossy. The clay coating is brittle and can crack when the paper is bent. Consequently, Carbon or silver ink paths applied directly to the clay coat could lose their electrical continuity. Application of Curable UV Coating to the clay coat prevents this. In Step 3, Resistors and Traces are printed with carbon or silver ink.

Step 4 involves applying another layer of Curable UV coating. This layer is applied on top of both carbon and silver inks and serves as an insulator to prevent electrical contact with outside sources other than the Tag. This coat also fills in the pores of the carbon and silver ink, serving as a bonding material. Self-adhesive paper or plastic tape can be used in conjunction with or in place of the coating. The Grid shown in FIG. 10.1 is obtained on completion of the four steps in FIG. 10.2.

Paper is not the only material on which the Grid can be printed. Paper label stock, polymer film and paper-backed foil can also be used.

A layer of adhesive is applied to the bottom surface of the paper, as shown in FIG. 10.3.

When the paper is heated, this adhesive melts and attaches the paper to other surfaces with which it is in contact. This process is explained in Step 15 hereinbelow.

The paper with its printed Grid is then die cut. FIG. 10.4 shows a die cut paper.

Referring back to FIG. B4, G_Switch 2 is opened intentionally to change the current's path. To open a switch on a Grid (see FIG. 10.1) a section of the conductive path must be broken completely. A person needs to apply pressure on a specific section of the Grid to break that section. This action is taken when a blister package of medication is placed inside the paper with the plastic blisters protruding through the die cut holes in the paper, and the paper is heat sealed to enclose the blister package. This process is described in Step 14.

The Grid is aligned with the individual blisters in such a way that pushing a tablet through the backing of the blister package will break the associated path of the Grid. This forces the current to take a resistive path. However, breakage of the conductive path may occur in other sections of the Grid if pressure is not applied properly. To facilitate breaking in the appropriate area of the Grid, die cutting is used to score patterns, as at 50, around areas of the Grid that are required to serve as switches. FIG. 10.4 shows a Die Cut Grid.

When a tablet is expelled from its blister, it breaks the path in the section of the Grid at the associated scored area. A semi-circular pattern of scores 50 prevents creases from forming on conductive paths when heat-sealed paper with an enclosed blister package is deformed. Creases cause resistance changes in the conductive paths, resulting in malfunction of the system. FIG. 10.5 shows a broken path with its associated score pattern.

The scoring pattern acts like a door, allowing the tablet to break the grid and slide out.

Step 11: Checking Grid Resistances

Once the paper Grid has been die cut, a unique ID Number is assigned to it. The Grid's resistances must then be verified. Grid resistances must fall into a range for that Grid to be acceptable.

The generation of an ID Number and verification of the Grid's resistances is done by proprietary software known as "Package Quality Assurance One" (PQA1) Software. PQA1 is installed on a PC with a Label Maker and a Multimeter connected to the PC. When launched, PQA1 automatically detects if the Label Maker and Multimeter are connected and operating. It also checks that a specific database and connection to it exist. This database contains all the ID Numbers for various types of paper substrate. Once PQA1 has verified that the peripherals and database are connected, it allows a user to enter the type of paper being checked. When the <Print> button is pressed, PQA1 retrieves a unique ID Number for that type of paper and generates a label, using Label Maker, with that number printed on it. This label also contains a barcode representing the ID Number. FIG. 11.1 shows a screenshot of a paper type entered into PQA1 software.

The Label is pasted on the paper adjacent to the Grid and shows the ID Number of that paper Grid. PQA1 completes Step 1 and progresses to Step 2, where it displays the unique ID Number and enables a user to measure the Grid's resistances.

A Grid preferably consists of two smaller grids 52, 54. The reason for dividing the Grid into sub-grids is that if one grid fails the other is not affected and the overall Grid would still operate. It also reduces the overall magnitude of resistance by half.

The resistances are measured using a Multimeter with its probes first placed on common and Grid 1 (52), and then on common and Grid 2 (54). Resistances are read automatically by the Multimeter and transmitted to PQA1 software. FIG. 11.2 shows a Grid and identifies the sub-grids and areas where the probes are placed.

PQA1 software accepts the measured resistances and checks to see whether these resistances fall into an acceptable range. If a resistance is outside the range PQA1 highlights that resistor's field in colour red. FIG. 11.3 shows a screenshot of PQA1 software with both steps completed.

When the <Submit> button is pressed, PQA1 records the resistances measured to a database with reference to that particular Grid ID Number.

Further Quality Assurance (QA) is conducted on 32-Dose and 18-Dose Grids by measuring each printed resistor. FIG. 11.4 shows a 32-Dose Grid with silver ink pads 56 printed on it to enable measurement of each resistor (black, carbon ink path).

The contact pad 56 divides each resistor into two parallel resistors. The resistance of an individual resistor can be determined by placing the two probes of a Multimeter on the adjacent contact pads. This procedure allows non-destructive testing of the Grid. A Nail Bed can be used to automate the procedure. Some conductive inks dry more slowly than others and during this process their conductivity will change. With such inks it is desirable to perform repeated resistance measurements during the first 3 to 4 weeks after printing, until stable resistances occur. For even slower drying inks it may be desirable to use such measurements to predict the ultimate resistances that will occur during the grid's useful life.

Each resistor value R obtained during such measurement is compared to the minimal allowable value, calculated as:

$$R_{min} > (R_{ref}/3) - 5\%$$

Failure to compare the individual resistors to the grid's reference resistor can introduce multiple undetected expulsion events. Making such comparisons at several points during the curing process will detect abnormal ink curing due to inconsistencies in the grid substrate.

When paper with a grid printed on it is bent the resistance of the grid changes. Such changes in resistance could cause the attached tag to record incorrect events. (The attachment method is described in Step 12). To address this problem, a second, mirror grid is printed on the obverse of the paper. Grids printed on both sides of the paper substrate provide a stable resistance value to the tag when the grid is bent.

Explanation of Resistance Variation:

Total resistance is based on the length of the resistor and the resistance per square unit of printed resistor. Equation E11.1 shows the relationship:

$$R_{Total}=Length*(R_\Omega/square) \tag{E11.1}$$

A resistor printed on paper is shown in cross-section in FIG. 11.5. The total resistance of this resistor (R1) is equivalent to its length (L1) multiplied by the resistance per square unit.

If the paper is bent convexly, as shown in FIG. 11.6, the total resistance (R1) of the Resistor will change since the length of the resistor increases. The new resistance R2 is greater than R1.

Conversely, if the grid is bent concavely the resistor's length is decreased and total resistance R3 will be less than R1. This is illustrated in FIG. 11.7.

If a mirror grid is printed on the back of the paper substrate, bending will cause R2 to increase on one side and R3 to decrease on the other, giving the expected resistance R1. The two grids on opposite sides of the paper must both be in electrical continuity with the tag as illustrated in FIG. 11.8. The equivalent circuit created by this method is shown in FIG. 11.9.

Step 12: Stitching Paper with a Tag

Grids passing QA and having unique ID Numbers attached progress to a stitching station. Here, a Brother™ BAS-311F-0 Automated Stitching Machine 57 (FIG. 12.1) attaches the tag to the appropriate points of the printed grid using silver conductive thread. FIG. 12.2 shows a tag 10 stitched to a grid 44 via conductive stitching 58.

Each stitching procedure is inspected visually and any loose conductive fibers are removed and a protective self-adhesive label is applied.

A tag stitched to a grid records the time of any significant resistance change in the grid. The applicant implements a unique method to calculate precise time, as discussed below.

Calculation of Time by the Tag

Time calculated by the PC is assumed to be accurate as it is synchronized with an Atomic Clock. The PC's clock is updated at interval $T_1$ of every second. After 60 intervals, the PC updates the minute counter. The tag 10 uses an oscillator 20 containing a crystal resonator to calculate time. The oscillator updates the tag's clock every interval $T_2$. In general, the accuracy of the time calculated by the oscillator is determined by the quality of the crystal resonator. $T_2$ is 1 second plus or minus delta $\Delta$. Delta $\Delta$ is the error introduced by the crystal resonator. FIG. 12.3 shows the PC's accurate time interval $T_1$ of one second and the oscillator's time interval $T_2$.

Equation E12.1 shows the relationship between $T_1$ and $T_2$.

$$T_1=T_2\pm delta\,\Delta \tag{E12.1}$$

If the crystal resonator is of good quality, delta $\Delta$, will be small. However, accurate crystal resonators are expensive, as they require time to calibrate to the correct frequency.

To reduce delta $\Delta$, a method that uses the firmware on the reader to calculate the precise time recorded by the tag has been developed. This method adjusts the interval $T_2$ of the oscillator so the counter incremented at $T_2$ coincides with the CPU clock counter change. When a tag is scanned on a reader, the reader records the time on its clock and the tag's counter value and notes them as $T_{sync1}$ and $N_{local1}$, respectively. When the tag is scanned again, the reader again records its clock time and stores the counter value of the tag. These values are noted as $T_{sync2}$ and $N_{local2}$.

The reader applies equation E12.2 to calculate the $T_2$ value by which the tag's oscillator should be adjusted.

$$T_{2new}=(T_{sync2}-T_{sync1})/(N_{local2}-N_{local1}) \tag{E12.2}$$

The reader uses $T_{2new}$ and equation E12.3 to adjust all the times recorded by the tag. Individual event times recorded by the tag are denoted as $T_{event}$.

$$T_{event}=T_{sync1}+(\text{tag's counter})*T_{2new} \tag{E12.3}$$

Step 13: Checking the Connection Between the Tag and the Grid

A stitched tag and grid forms an electronic circuit as shown in FIG. B1. To verify that this circuit has been created the connection between the tag and the grid must be verified. The tag's internal components such as the timer must also be tested.

Proprietary "Package Quality Assurance 2" (PQA2) software does these tests. PQA2 requires a barcode scanner, Certscan™ reader, and digital camera to be connected to the PC on which is installed PQA2. PQA2 is launched and a stitched grid and tag unit is placed on the Certiscan™ reader. While on the reader the barcode label attached to the grid's substrate is scanned by the barcode scanner. PQA2 receives the scanned result, which is the ID Number of that grid, and checks with the database to confirm it is a valid ID Number. If the check fails, PQA2 notifies the operator of the problem and requests the next grid and tag unit for scanning. If the ID Number is valid, PQA2 sets the tag's ID Number to match the grid's ID Number. It also tests the tag's microcontroller timer, instructs tag to measure the grid resistances, and compares these measured resistances with a predefined resistance range and with the resistances determined by PQA1.

If all operations are successful, PQA2 judges this grid and tag assembly acceptable for use and displays "PASS" on its screen. FIG. 13.1 shows a screenshot of a stitched paper judged as "PASS" by PQA2. If any of the operations fail, PQA2 prohibits the user from using that grid and tag unit and displays "FAIL" on its screen.

Regardless of Pass or Fail status, a digital image of the grid and tag unit is taken automatically by PQA2 for future reference. PQA2 then permits the user to save all the results of its operations by pressing <Submit>. Once <Submit> is pressed, PQA2 saves all its results to the database with reference to the grid and tag unit ID Number. FIG. 13.2 shows a PQA2 workstation with the peripherals attached to the PC and PQA2 software operating.

Step 14: Inserting the Blister Package into the Stitched Paper

A blister package containing medication is inserted into a stitched grid and tag unit. The type of paper used depends on the type of blister package being inserted. FIG. 14.1 shows the front and back of a 14-Dose blister package.

A 14-Dose paper grid is required to accommodate a 14-Dose blister package. The paper grid 60 has cut outs with precise dimensions and locations that allow a blister package to be inserted. FIG. 14.2 shows a 14-Dose paper with and without a blister package inserted.

The paper substrate is folded to create a package containing the grid, attached tag, and blister package. FIG. 14.3 shows and describes the steps to fold the paper substrate. The end result is a compact package containing all essential elements, namely the blister package with its pills, capsules or other medication held within individual blisters, and the grid adhered to the back of the blister package so that a conductive trace is ruptured when the contents of a blister are expelled therefrom, allowing the tag to record the time and any other relevant information.

Step 15: Heat-Sealing

The folded paper in Step 5 of FIG. 14.3 contains a blister package and stitched tag. The folded paper is now heat-sealed to create a functional package. The folded paper is placed in a heat-seal machine 62 at 320° Fahrenheit for 7 seconds. FIG. 15.1 shows a view of the heat-seal machine 62.

The temperature of Heat-Seal machine is set by a dial on the machine. A temperature gauge indicates the current temperature. A lever closes the top over the bottom.

The foregoing has described the steps involved in the production of a Med-ic™ ECM tag. It is understood that variations in the method could be effected without departing from the spirit of the invention. It is also understood that the present method could be applied to other products of a similar nature.

The invention claimed is:

1. A method for manufacturing a conductive grid for attachment to a blister package such that expulsion of an article from a blister of said package will rupture a conductive trace included as a component of said grid, comprising the steps of:
    preparing an electronic tag having at least microcontroller means, capacitor means, oscillator means, resistor means and diode means thereon;
    transferring tag identification information to said microcontroller means;
    installing battery power means to said tag for providing electrical power to said microcontroller means;
    verifying the integrity of said tag and the components
    printing a predetermined pattern of conductive traces on a substrate, said pattern being adapted to place said traces in alignment with the blisters of the blister package;
    verifying resistance levels associated with said traces to ensure that the resistance levels are within predetermined limits;
    permanently connecting the tag to said grid such that defined connection points of said tag are conductively connected to defined portions of said traces;
    verifying the integrity of the grid including the conductive traces and the tag; and
    making the grid available for assembly to the blister package.

2. The method of claim 1 wherein said preparing step includes a step of printing a sheet of PCB's comprising of a plurality of printed circuit boards (PCB's) on a prepared sheet of suitable material, each said PCB being defined by a predetermined circuit incorporating said microcontroller means, capacitor means, oscillator means, resistor means and diode means as well as a location for said battery means, and each said PCB also including a plurality of holes extending therethrough.

3. The method of claim 2 wherein said transferring step includes the steps of locating said sheet of PCB's in a nail bed portion of firmware writing apparatus, contacting specific contact points on each PCB of said sheet with pin means associated with said firmware writing apparatus, and burning said tag identification information from said apparatus to each said microcontroller means.

4. The method of claim 3 wherein said tag identification information includes a unique tag identification number for each PCB and identification of the firmware version written to each PCB.

5. The method of claim 4 wherein said firmware writing apparatus also verifies calibration of said oscillator means and automatically marks any PCB which was not successfully programmed by said apparatus.

6. The method of claim 2 wherein said battery power means is installed to each said PCB by soldering.

7. The method of claim 2 including a step of applying a layer of protective foam material to cover at least one surface of said sheet.

8. The method of claim 7 including a step of applying a layer of foam material to the surface of said sheet opposite said at least one surface.

9. The method of claim 2 including a step of separating said sheet into individual tags, each tag having its own unique identification information associated therewith.

10. The method of claim 1 wherein said verifying the integrity of said tag step further comprises a step of verifying available life for said battery power means utilizing battery test firmware written to the microcontroller means of randomly selected tags, the battery test firmware recording a reading of energy and voltage level at regular intervals for display on reading apparatus when prompted, so as to monitor the performance of battery power means for specific batches of tags over an extended period of time.

11. The method of claim 10 wherein each said randomly selected tag has a reference resistor connected thereto for voltage measurements over said extended period of time.

12. The method of claim 10 wherein said verifying the integrity of said tag step further comprises a step of checking for time accuracy and battery voltage means, and the marking of any tags which fail to meet predetermined minimum standards.

13. The method of claim 1 wherein said predetermined pattern of traces applied to the substrate defines a printed sensor grid (PSG) to which the tag is applied after verification of the integrity and the adhesive is applied to the opposite surface of said PSG.

14. The method of claim 13 wherein said substrate has first and second opposing surfaces and said pattern of traces includes conductive and resistive paths which are printed on the first surface of the substrate using silver-based and carbon-based inks respectively, the printing step including the application of a first curable ultraviolet (UV) coating to the substrate, the application of the pattern of traces using the appropriate ink, and the application of a second coating of curable UV coating, said first UV coating serving to make the substrate more uniform and resistant to temperature and humidity effects and also improving the flexibility of the substrate, and said second UV coating serving to protect said printed inks and to prevent unwanted contact with external sources of electricity.

15. The method of claim 14 wherein said substrate is selected from the group of substrates consisting of paper, paper label stock, polymer film and paper-backed foil.

16. The method of claim 14 further comprising a step of applying a layer of a heat-sensitive adhesive to the second surface of said substrate.

17. The method of claim 14 wherein said substrate is commercial label stock having a self-adhesive coating on the surface thereof opposite said one surface carrying said conductive and resistive traces thereon.

18. The method of claim 14 further comprising a step of die-cutting a region in the substrate adjacent said traces in the area where the blister of the blister package will be located so as to provide a series of score lines in the substrate, facilitating the rupturing of a trace during expulsion of an article from the blister.

19. The method of claim 14 wherein said step of connecting the tag to the PSG includes the step of positioning the tag on the substrate so that contact points of said tag are adjacent predetermined contact points associated with said traces, and stitching said tag to said substrate utilizing conductive thread.

20. The method of claim 19 wherein following the stitching of said tag to the PSG the integrity of the connection is verified as is said oscillator means within said microcontroller means and the resistance levels of the conductive traces on said PSG.

21. The method of claim 20 further comprising a step of applying an identifying barcode to each tag and PSG assembly that passes all tests and photographing each assembly, including all identifying data printed or presented thereon.

22. The method of claim 21 further comprising a step of positioning an acceptable tag and PSG assembly according to claim 16 against a comparable surface of the blister package with the heat-sensitive adhesive on said substrate abutting said blister package surface and activating said heat-sensitive adhesive for a time sufficient to cause the adhesive to melt momentarily, so as to adhere the tag and PSG assembly to the blister package.

23. The method of claim 21 further comprising a step of applying an acceptable tag and PSG assembly according to claim 17 against a comparable surface of the blister package with the adhesive coating on said substrate adhering said tag and PSG assembly to said blister package.

24. A method for manufacturing blister packages provided with one or more conductive grids on a surface thereof such that expulsion of an article from a blister will rupture a conductive trace included as a component of said grid, comprising the steps of:
  preparing an electronic tag having at least microcontroller means, capacitor means, oscillator means, resistor means and diode means thereon;
  transferring tag identification information to said microcontroller means;
  installing battery power means to said tag for providing electrical power to said microcontroller means;
  verifying the integrity of said tag and the components carried thereon;
  printing a predetermined pattern of conductive traces on a substrate, said pattern being adapted to place said traces in alignment with the blisters of the blister package;
  verifying resistance levels associated with said traces to ensure that they are within predetermined limits;
  permanently connecting the tag to said grid such that defined connection points of said tag are conductively connected to defined portions of said traces;
  verifying the integrity of the grid including the conductive traces and the tag; and
  connecting the grid to the blister package so that each conductive trace of said grid is in alignment with a selected blister of said package, whereby rupture of a trace associated with a particular blister will provide a signal to said tag, allowing the microcontroller means carried by the tag to record the time of occurrence of the rupture event.

* * * * *